United States Patent [19]

Belagaje

[11] Patent Number: 5,378,613
[45] Date of Patent: Jan. 3, 1995

[54] METHOD FOR INCREASED EXPRESSION OF LOW MOLECULAR WEIGHT RECOMBINANT POLYPEPTIDES

[75] Inventor: Rama M. Belagaje, Indianapolis, Ind.

[73] Assignee: Eli Lilly and Company, Indianapolis, Ind.

[21] Appl. No.: 764,655

[22] Filed: Sep. 24, 1991

[51] Int. Cl.$^6$ .................. C12N 15/00; C12N 1/21; C12N 15/17; C12N 15/18

[52] U.S. Cl. .................. 435/69.7; 435/69.4; 435/69.1

[58] Field of Search .......... 435/69.1, 69.4, 69.7, 435/320.1, 252.3, 252.33; 536/27, 23.4, 23.5, 23.51; 935/33, 38

[56] References Cited

U.S. PATENT DOCUMENTS

| | | | |
|---|---|---|---|
| 4,782,139 | 11/1988 | DeMarchi et al. | 530/407 |
| 5,158,875 | 10/1992 | Miller et al. | 435/69.1 |
| 5,304,473 | 4/1994 | Belagaje et al. | 435/69.7 |

FOREIGN PATENT DOCUMENTS

| | | |
|---|---|---|
| 0361956 | 4/1990 | European Pat. Off. |
| WO88/10299 | 12/1988 | WIPO |
| WO91/02807 | 3/1991 | WIPO |

OTHER PUBLICATIONS

Looman, A. C. et al., *EMBO J*, 6(8):2489–92, 1987.

DiMarchi, R. D. et al., *J. Cell. Biochem.*, Supplement 12B, p. 58, V024.

Hsiung, H. M. et al., *Methods in Enzymology*, 153:390–401, 1987.

Cantrell et al., Effects of second-codon on expression of the insulin-like growth factor-II-encoding gene in *Escherichia coli*, *Gene*, 98:217-23, (1991).

Buell et al., Optimizing the expression in *E. coli* of a synthetic gene encoding somatomedin-C (IGF-I), *Nucleic Acids Research*, 13:1923-38 (1985).

Wong et al., Expression of insulin-like growth factor-I in *Escherichia coli*, *Gene*, 68:193-203 (1988).

Saito et al., Production and Isolation of Recombinant Somatomedin C, *J. Biochem.* 101:123–134 (1987).

Primary Examiner—Garnette D. Draper
Assistant Examiner—Marianne Porta Allen
Attorney, Agent, or Firm—Paul R. Cantrell; Gerald V. Dahling

[57] ABSTRACT

The present invention provides a method for increasing expression of low molecular weight polypeptides which are produced by recombinant DNA tranformation of prokaryotic host cells. This invention allows the direct expression of these polypeptides without fusion to an otherwise expressible protein and requires only the addition of a single amino acid to the sequence of the polypeptide product of interest.

8 Claims, 12 Drawing Sheets

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..51
        ( D ) OTHER INFORMATION: The NNN codon at position 4-7 encodes amino acids as defined in the specification. The last two nucleotides of the sequence are the first two nucleotides of the codon for Gln when this sequence is ligated as defined in the specification.

( x i ) SEQUENCE DESCRIPTION: SEQ ID NO:1:

```
T ATG NNN GGC CCG GAA ACT CTG TGC GGC GCT GAA CTG GTT GAC GCT CTG CA    51
  Met Xaa Gly Pro Glu Thr Leu Cys Gly Ala Glu Leu Val Asp Ala Leu
   1       5                      10                  15
```

( 2 ) INFORMATION FOR SEQ ID NO:2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( D ) OTHER INFORMATION: The NNN nucleotides at positions 41-43 are the complement to the NNN nucleotides in SEQ ID NO:1

( x i ) SEQUENCE DESCRIPTION: SEQ ID NO:2:

```
GAGCGTCAAC CAGTTCAGCG CCGCACAGAG TTTCCGGGCC NNNCA                        45
```

( 2 ) INFORMATION FOR SEQ ID NO:3:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 18..44

( x i ) SEQUENCE DESCRIPTION: SEQ ID NO:3:

```
TCTAGAGGGT ATTAATA ATG TAT ATT GAT TTT AAT AAG GAG GAA TAATCAT          51
                   Met Tyr Ile Asp Phe Asn Lys Glu Glu
                    1               5
```

( 2 ) INFORMATION FOR SEQ ID NO:4:

( i ) SEQUENCE CHARACTERISTICS:
        ( A ) LENGTH: 49 base pairs
        ( B ) TYPE: nucleic acid (C) STRANDEDNESS: single
(D) TOPOLOGY: linear (ii) MOLECULE TYPE: DNA (genomic)

(ix) FEATURE:
(A) NAME/KEY: CDS
(B) LOCATION: 17..43

(xi) SEQUENCE DESCRIPTION: SEQ ID NO:4:

```
CTAGAGGGTA TTAATA ATG TAT ATT GAT TTT AAT AAG GAG GAA TAATCA         49
              Met Tyr Ile Asp Phe Asn Lys Glu Glu
               1               5
```

(2) INFORMATION FOR SEQ ID NO:5:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

```
TATGATTATT CCTCCTTATT AAAATCAATA TACATTATTA ATACCCT                   47
```

(2) INFORMATION FOR SEQ ID NO:6:

(i) SEQUENCE CHARACTERISTICS:
(A) LENGTH: 601 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 2..598

(xi) SEQUENCE DESCRIPTION: SEQ ID NO:6:

```
T ATG TTC CCA TTG GAT GAT GAT GAT AAG TTC CCA GCC ATG TCC TTG         46
  Met Phe Pro Leu Asp Asp Asp Asp Lys Phe Pro Ala Met Ser Leu
   1               5                  10                  15

TCC GGC CTG TTT GCC AAC GCT GTG CTC CGG GCT CAG CAC CTG CAT CAG       94
Ser Gly Leu Phe Ala Asn Ala Val Leu Arg Ala Gln His Leu His Gln
               20                  25                  30

CTG GCT GCT GAC ACC TTC AAA GAG TTT GAG CGC ACC TAC ATC CCG GAG      142
Leu Ala Ala Asp Thr Phe Lys Glu Phe Glu Arg Thr Tyr Ile Pro Glu
               35                  40                  45

GGA CAG AGA TAC TCC ATC CAG AAC ACC CAG GTT GCC TTC TGC TTC TCT      190
Gly Gln Arg Tyr Ser Ile Gln Asn Thr Gln Val Ala Phe Cys Phe Ser
           50                  55                  60

GAA ACC ATC CCG GCC CCC ACG GGC AAG AAT GAG GCC CAG CAG AAA TCA      238
Glu Thr Ile Pro Ala Pro Thr Gly Lys Asn Glu Ala Gln Gln Lys Ser
 65                  70                  75

GAC TTG GAG CTG CTT CGC ATC TCA CTG CTC CTC ATC CAG TCG TGG CTT      286
Asp Leu Glu Leu Leu Arg Ile Ser Leu Leu Leu Ile Gln Ser Trp Leu
 80                  85                  90                  95

GGG CCC CTG CAG TTC CTC AGC AGA GTC TTC ACC AAC AGC TTG GTG TTT      334
Gly Pro Leu Gln Phe Leu Ser Arg Val Phe Thr Asn Ser Leu Val Phe
                100                 105                 110

GGC ACC TCG GAC CGT GTC TAT GAG AAG CTG AAG GAC CTG GAG GAA GGC      382
Gly Thr Ser Asp Arg Val Tyr Glu Lys Leu Lys Asp Leu Glu Glu Gly
                115                 120                 125

ATC CTG GCC CTG ATG CGG GAG CTG GAA GAT GGC ACC CCC CGG GCT GGG      430
Ile Leu Ala Leu Met Arg Glu Leu Glu Asp Gly Thr Pro Arg Ala Gly
               130                 135                 140
```

| | | | | | | | | | | | | | | | | |
|---|---|---|---|---|---|---|---|---|---|---|---|---|---|---|---|---|
| CAG | ATC | CTC | AAG | CAG | ACC | TAT | GAC | AAA | TTT | GAC | ACA | AAC | ATG | CGC | AGT | 478 |
| Gln | Ile | Leu | Lys | Gln | Thr | Tyr | Asp | Lys | Phe | Asp | Thr | Asn | Met | Arg | Ser | |
| | 145 | | | | 150 | | | | | 155 | | | | | | |
| GAC | GAC | GCG | CTG | CTC | AAG | AAC | TAC | GGT | CTG | CTC | TCC | TGC | TTC | CGG | AAG | 526 |
| Asp | Asp | Ala | Leu | Leu | Lys | Asn | Tyr | Gly | Leu | Leu | Ser | Cys | Phe | Arg | Lys | |
| 160 | | | | | 165 | | | | | 170 | | | | | 175 | |
| GAC | CTG | CAT | AAG | ACG | GAG | ACG | TAC | CTG | AGG | GTC | ATG | AAG | TGC | CGC | CGC | 574 |
| Asp | Leu | His | Lys | Thr | Glu | Thr | Tyr | Leu | Arg | Val | Met | Lys | Cys | Arg | Arg | |
| | | | | 180 | | | | | 185 | | | | | 190 | | |
| TTC | GGG | GAG | GCC | AGC | TGT | GCC | TTC | TAG | | | | | | | | 601 |
| Phe | Gly | Glu | Ala | Ser | Cys | Ala | Phe | | | | | | | | | |
| | | | | 195 | | | | | | | | | | | | |

( 2 ) INFORMATION FOR SEQ ID NO:7:

( i ) SEQUENCE CHARACTERISTICS:
        ( A ) LENGTH: 603 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---|
| GATCCTAGAA | GGCACAGCTG | GCCTCCCCGA | AGCGGCGGCA | CTTCATGACC | CTCAGGTACG | 60 |
| TCTCCGTCTT | ATGCAGGTCC | TTCCGGAAGC | AGGAGAGCAG | ACCGTAGTTC | TTGAGCAGCG | 120 |
| CGTCGTCACT | GCGCATGTTT | GTGTCAAATT | TGTCATAGGT | CTGCTTGAGG | ATCTGCCCAG | 180 |
| CCCGGGGGGT | GCCATCTTCC | AGCTCCCGCA | TCAGGGCCAG | GATGCCTTCC | TCCAGGTCCT | 240 |
| TCAGCTTCTC | ATAGACACGG | TCCGAGGTGC | CAAACACCAA | GCTGTTGGTG | AAGACTCTGC | 300 |
| TGAGGAACTG | CAGGGGCCCA | AGCCACGACT | GGATGAGGAG | CAGTGAGATG | CGAAGCAGCT | 360 |
| CCAAGTCTGA | TTTCTGCTGG | GCCTCATTCT | TGCCCGTGGG | GGCCGGGATG | GTTTCAGAGA | 420 |
| AGCAGAAGGC | AACCTGGGTG | TTCTGGATGG | AGTATCTCTG | TCCCTCCGGG | ATGTAGGTGC | 480 |
| GCTCAAACTC | TTTGAAGGTG | TCAGCAGCCA | GCTGATGCAG | GTGCTGAGCC | CGGAGCACAG | 540 |
| CGTTGGCAAA | CAGGCCGGAC | AAGGACATGG | CTGGGAACTT | ATCATCATCA | TCCAATGGGA | 600 |
| ACA | | | | | | 603 |

( 2 ) INFORMATION FOR SEQ ID NO:8:

( i ) SEQUENCE CHARACTERISTICS:
        ( A ) LENGTH: 237 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 22..231

( x i ) SEQUENCE DESCRIPTION: SEQ ID NO:8:

| | | | | | | | | | | | | |
|---|---|---|---|---|---|---|---|---|---|---|---|---|
| AGCTTGGATG | ATGATGATAA G | GGC | CCG | GAA | ACT | CTG | TGC | GGC | GCT | GAA | CTG | 51 |
| | | Gly | Pro | Glu | Thr | Leu | Cys | Gly | Ala | Glu | Leu | |
| | | 1 | | | 5 | | | | | | 10 | |
| GTT | GAC | GCT | CTG | CAG | TTC | GTT | TGC | GGC | GAC | CGT | GGC | TTC | TAC | TTC | AAC | 99 |
| Val | Asp | Ala | Leu | Gln | Phe | Val | Cys | Gly | Asp | Arg | Gly | Phe | Tyr | Phe | Asn | |
| | | | | 15 | | | | | 20 | | | | | 25 | | |
| AAA | CCG | ACT | GGC | TAC | GGC | TCT | TCT | TCT | CGT | CGT | GCT | CCG | CAG | ACT | GGC | 147 |
| Lys | Pro | Thr | Gly | Tyr | Gly | Ser | Ser | Ser | Arg | Arg | Ala | Pro | Gln | Thr | Gly | |
| | | | 30 | | | | | 35 | | | | | 40 | | | |

| ATC | GTC | GAC | GAA | TGC | TGC | TTC | CGT | TGT | TGC | GAC | CTG | CGT | CGT | CTG | GAA | 195 |
| Ile | Val | Asp | Glu | Cys | Cys | Phe | Arg | Cys | Cys | Asp | Leu | Arg | Arg | Leu | Glu | |
| | | | 45 | | | | 50 | | | | 55 | | | | | |

| ATG | TAC | TGC | GCT | CCG | CTG | AAA | CCT | GCT | AAA | TCT | GCT | TAATAG | | | | 237 |
| Met | Tyr | Cys | Ala | Pro | Leu | Lys | Pro | Ala | Lys | Ser | Ala | | | | | |
| | 60 | | | | 65 | | | | 70 | | | | | | | |

( 2 ) INFORMATION FOR SEQ ID NO:9:

( i ) SEQUENCE CHARACTERISTICS:
    ( A ) LENGTH: 237 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

| GATCCTATTA | AGTAGATTTA | GCAGGTTTCA | GCGGAGCGCA | GTACATTTCC | AGACGACGCA | 60 |
| GGTCGCAACA | ACGGAAGCAG | CATTCGTCGA | CGATGCCAGT | CTGCGGAGCA | CGACGAGAAG | 120 |
| AAGAGCCGTA | GCCAGTCGGT | TTGTTGAAGT | AGAAGCCACG | GTCGCCGCAA | ACGAACTGCA | 180 |
| GAGCGTCAAC | CAGTTCAGCG | CCGCACAGAG | TTTCCGGGCC | CTTATCATCA | TCATCCA | 237 |

( 2 ) INFORMATION FOR SEQ ID NO:10:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 2..51
    ( D ) OTHER INFORMATION: The last two nucleotides of the
sequence are the first two nucleotides of the codon for Gln when this
sequence is ligated as defined in the specification.

( x i ) SEQUENCE DESCRIPTION: SEQ ID NO:10:

| T | ATG | CGT | GGC | CCG | GAA | ACT | CTG | TGC | GGC | GCT | GAA | CTG | GTT | GAC | GCT | 46 |
| | Met | Arg | Gly | Pro | Glu | Thr | Leu | Cys | Gly | Ala | Glu | Leu | Val | Asp | Ala | |
| | 1 | | | | 5 | | | | 10 | | | | | 15 | | |

| CTG | CA | 51 |
| Leu | | |

( 2 ) INFORMATION FOR SEQ ID NO:11:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

| GAGCGTCAAC | CAGTTCAGCG | CCGCACAGAG | TTTCCGGGCC | ACGCA | 45 |

( 2 ) INFORMATION FOR SEQ ID NO:12:

( i ) SEQUENCE CHARACTERISTICS:
    ( A ) LENGTH: 281 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 9..272

( x i ) SEQUENCE DESCRIPTION: SEQ ID NO:12:

```
AGCTTCAT ATG TAT TTT GTT AAC CAA CAC CTG TGC GGC TCC CAC CTG GTG          50
         Met Tyr Phe Val Asn Gln His Leu Cys Gly Ser His Leu Val
          1           5                  10

GAA GCT CTG TAC CTG GTG TGC GGT GAA CGT GGC TTC TTC TAC ACC CCG           98
Glu Ala Leu Tyr Leu Val Cys Gly Glu Arg Gly Phe Phe Tyr Thr Pro
 15              20                  25                  30

AAG ACC CGC CGT GAG GCA GAG GAC CTG CAG GTG GGT CAG GTG GAG CTG          146
Lys Thr Arg Arg Glu Ala Glu Asp Leu Gln Val Gly Gln Val Glu Leu
                 35                  40                  45

GGC GGT GGC CCG GGT GCA GGC AGC CTG CAG CCG CTG GCC CTG GAG GGT          194
Gly Gly Gly Pro Gly Ala Gly Ser Leu Gln Pro Leu Ala Leu Glu Gly
             50                  55                  60

TCC CTG CAG AAG CGT GGC ATT GTG GAA CAA TGC TGT ACC AGC ATC TGC          242
Ser Leu Gln Lys Arg Gly Ile Val Glu Gln Cys Cys Thr Ser Ile Cys
         65                  70                  75

TCC CTG TAC CAG CTG GAG AAC TAC TGC AAC TAGGATCCG                        281
Ser Leu Tyr Gln Leu Glu Asn Tyr Cys Asn
         80                  85
```

( 2 ) INFORMATION FOR SEQ ID NO:13:

( i ) SEQUENCE CHARACTERISTICS:
        ( A ) LENGTH: 281 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
AATTCGGATC CTAGTTGCAG TAGTTCTCCA GCTGGTACAG GGAGCAGATG CTGGTACAGC         60
ATTGTTCCAC AATGCCACGC TTCTGCAGGG AACCCTCCAG GGCCAGCGGC TGCAGGCTGC        120
CTGCACCCGG GCCACCGCCC AGCTCCACCT GACCCACCTG CAGGTCCTCT GCCTCACGGC        180
GGGTCTTCGG GGTGTAGAAG AAGCCACGTT CACCGCACAC CAGGTACAGA GCTTCCACCA        240
GGTGGGAGCC GCACAGGTGT TGGTTAACAA AATACATATG A                           281
```

( 2 ) INFORMATION FOR SEQ ID NO:14:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..40
        ( D ) OTHER INFORMATION:

( x i ) SEQUENCE DESCRIPTION: SEQ ID NO:14:

```
T ATG CGT TTT GTT AAC CAA CAC CTG TGC GGC TCC CAC CTG                    40
  Met Arg Phe Val Asn Gln His Leu Cys Gly Ser His Leu
   1           5                  10
```

( 2 ) INFORMATION FOR SEQ ID NO:15:

( i ) SEQUENCE CHARACTERISTICS:
        ( A ) LENGTH: 35 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:15:

GTGGGAGCCG CACAGGTGTT GGTTAACAAA ACGCA                35

(2) INFORMATION FOR SEQ ID NO:16:

(i) SEQUENCE CHARACTERISTICS:
      (A) LENGTH: 115 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 2..115

(xi) SEQUENCE DESCRIPTION: SEQ ID NO:16:

```
T ATG CGT ATG TTT GTT AAC CAA CAC CTG TGC GGC TCC CAC CTG GTG         46
  Met Arg Met Phe Val Asn Gln His Leu Cys Gly Ser His Leu Val
  1               5                  10                   15

GAA GCT CTG TAC CTG GTG TGC GGT GAA CGT GGC TTC TTC TAC ACC AAG       94
Glu Ala Leu Tyr Leu Val Cys Gly Glu Arg Gly Phe Phe Tyr Thr Lys
                 20              25                  30

CCG ACC CGC CGT GAG GCA GAG                                          115
Pro Thr Arg Arg Glu Ala Glu
             35
```

(2) INFORMATION FOR SEQ ID NO:17:

(i) SEQUENCE CHARACTERISTICS:
      (A) LENGTH: 116 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:17:

GTCCTCTGCC TCACGGCGGG TCGGCTTGGT GTAGAAGAAG CCACGTTCAC CGCACACCAG     60

GTACAGAGCT TCCACCAGGT GGGAGCCGCA CAGGTGTTGG TTAACAAACA TACGCA        116

(2) INFORMATION FOR SEQ ID NO:18:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 2..40

(xi) SEQUENCE DESCRIPTION: SEQ ID NO:18:

```
T ATG CGT TTT GTT AAC CAA CAC CTG TGC GGC TCC CAC CTG                 40
  Met Arg Phe Val Asn Gln His Leu Cys Gly Ser His Leu
  1               5                  10
```

(2) INFORMATION FOR SEQ ID NO:19:

(i) SEQUENCE CHARACTERISTICS:
      (A) LENGTH: 35 base pairs
      (B) TYPE: nucleic acid
      (C) STRANDEDNESS: single ( D ) TOPOLOGY: linear ( i i ) MOLECULE TYPE: DNA (genomic)

( x i ) SEQUENCE DESCRIPTION: SEQ ID NO:19:

GTGGGAGCCG CACAGGTGTT GGTTAACAAA ACGCA  35

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..40

( x i ) SEQUENCE DESCRIPTION: SEQ ID NO:20:

```
T ATG CGT TTT GTT AAC CAA CAC CTG TGC GGC TCC GAC CTG           40
  Met Arg Phe Val Asn Gln His Leu Cys Gly Ser Asp Leu
  1               5                   10
```

( 2 ) INFORMATION FOR SEQ ID NO:21:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GTCGGAGCC GCACAGGTGT TGGTTAACAA AACGCA  35

( 2 ) INFORMATION FOR SEQ ID NO:22:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..72

( x i ) SEQUENCE DESCRIPTION: SEQ ID NO:22:

```
GTG GAA GCT CTG TAC CTG GTG TGC GGT GAA CGT GGC TTC TTC TAC ACC   48
Val Glu Ala Leu Tyr Leu Val Cys Gly Glu Arg Gly Phe Phe Tyr Thr
1               5                   10                  15

CCG AAG ACG CGT CGT GAG GCA GAG                                   72
Pro Lys Thr Arg Arg Glu Ala Glu
                20
```

( 2 ) INFORMATION FOR SEQ ID NO:23:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GTCCTCTGCC TCACGACGCG TCTTCGGGGT GTAGAAGAAG CCACGTTCAC CGCACACCAG    60

GTACAGAGCT TCCACCAG    78

( 2 ) INFORMATION FOR SEQ ID NO:24:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..74
    ( D ) OTHER INFORMATION: The first two nucleotides of the
sequence are the last two nucleotides of the codon for Thr when this
sequence is ligated as defined in the specification.

( x i ) SEQUENCE DESCRIPTION: SEQ ID NO:24:

```
CG CGT CGT CGT GCC ATT GTG GAA CAA TGC TGT ACC AGC ATC TGC TCC           47
   Arg Arg Arg Gly Ile Val Glu Glu Cys Cys Thr Ser Ile Cys Ser
    1           5               10                  15

CTG TAC CAG CTG GAG AAC TAC TGC AAC TAG                                  77
Leu Tyr Gln Leu Glu Asn Tyr Cys Asn
              20
```

( 2 ) INFORMATION FOR SEQ ID NO:25:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:25:

GATCCTAGTT GCAGTAGTTC TCCAGCTGGT ACAGGGAGCA GATGCTGGTA CAGCATTGTT    60

CCACAATGGC ACGACGA    77

( 2 ) INFORMATION FOR SEQ ID NO:26:

( i ) SEQUENCE CHARACTERISTICS:
    ( A ) LENGTH: 214 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 2..208

( x i ) SEQUENCE DESCRIPTION: SEQ ID NO:26:

```
T ATG CGT GCT TAT CGA CCG TCT GAA ACT CTG TGC GGC GGC GAA CTG            46
  Met Arg Ala Tyr Arg Pro Ser Glu Thr Leu Cys Gly Gly Glu Leu
   1           5               10                  15

GTT GAC ACT CTG CAG TTC GTT TGC GGC GAC CGT GGC TTC TAC TTC TCT          94
Val Asp Thr Leu Gln Phe Val Cys Gly Asp Arg Gly Phe Tyr Phe Ser
                  20                  25                  30

CGT CCG GCT TCT CGT GTT TCT AGG CGT TCT CGT GGC ATC GTT GAA GAA         142
Arg Pro Ala Ser Arg Val Ser Arg Arg Ser Arg Gly Ile Val Glu Glu
              35                  40                  45

TGC TGC TTC CGT TCT TGC GAC CTG GCT CTG CTG GAA ACT TAC TGC GCT         190
Cys Cys Phe Arg Ser Cys Asp Leu Ala Leu Leu Glu Thr Tyr Cys Ala
              50                  55                  60

ACT CCA GCT AAA TCT GAA TAATAG                                          214
```

Thr Pro Ala Lys Ser Glu
    65

(2) INFORMATION FOR SEQ ID NO:27:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
GATCCTATTA  TTCAGATTTA  GCTGGAGTAG  CGCAGTAAGT  TTCCAGCAGA  GCCAGGTCGC    60
AAGAACGGAA  GCAGCATTCT  TCAACGATGC  CACGAGAACG  CCTAGAAACA  CGAGAAGCCG   120
GACGAGAGAA  GTAGAAGCCA  CGGTCGCCGC  AAACGAACTG  CAGAGTGTCA  ACCAGTTCGC   180
CGCCGCACAG  AGTTTCAGAC  GGTCGATAAG  CACGCA                               216
```

METHOD FOR INCREASED EXPRESSION OF LOW MOLECULAR WEIGHT RECOMBINANT POLYPEPTIDES

BACKGROUND OF THE INVENTION

This invention falls within the art of recombinant DNA and genetic engineering technology. It provides a new process for increasing expression of polypeptides in transformed prokaryotic host cells.

The advent of recombinant DNA technology has made feasible the production of large amounts of many polypeptides that would not otherwise be possible by conventional chemical synthetic methods. However, the biosynthesis of some polypeptides in genetically altered host cells has proven difficult, especially those of low molecular weight. The method most common in the art for achieving suitable expression of these small polypeptides has been to fuse a DNA sequence, coding for the polypeptide product of interest, onto the DNA sequence of a second polypeptide which is readily expressed. This type of construction allows for the expression of a final product which is therefore a fused combination of the two polypeptides. The fused expression product is then cleaved and the desired polypeptide product of interest is isolated from the resulting mixture.

Direct expression of small polypeptides as non-fused expression products is often difficult to obtain for reasons not specifically known. Among reasons proposed for low expression levels of small polypeptides are the possible rapid degradation of these small polypeptides by the host cell or an impaired transcriptional or translational efficiency of the underlying coding sequence. Regardless of the explanation, polypeptide derivatives of the present invention have higher levels of expression than polypeptides which are expressed without the benefit of the present invention.

SUMMARY OF THE INVENTION

The present invention provides a method for producing polypeptide derivatives through the use of prokaryotic host cells which have been transformed by genetic engineering techniques. This invention demonstrates the general utility of increasing the direct expression levels of derivatives of polypeptide products of interest, altered only by the addition of a single amino acid to the sequence of the polypeptide product of interest that would otherwise be expressed. For purposes of this description, polypeptide products of interest are biologically active sequences of amino acids containing between about 10 and about 100 amino acid residues. The present invention comprises a method of producing a polypeptide derivative which comprises the structure Methionine-X-R, wherein X is selected from the group consisting of Alanine, Arginine, Glutamine, Glycine, Isoleucine, Leucine, Lysine, Methionine, Phenylalanine, Serine, Threonine, Tryptophan, or Valine, and R is the amino acid sequence of any polypeptide product of interest; in a prokaryotic host cell which has been transformed with a recombinant DNA vector, said vector comprising:

A. a DNA sequence that provides for autonomous replication or chromosomal integration of said vector in said host cell;

B. a promoter and translational activating sequence functional in said host cell; and C. a DNA compound which comprises the coding sequence of said polypeptide derivative, positioned in transcriptional phase with said promoter and translational activating sequence; said method comprising culturing said prokaryotic host cell under conditions suitable for gene expression.

DETAILED DESCRIPTION OF THE INVENTION

It is well known that the translational apparatus of prokaryotic cells requires an ATG initiation site in the DNA sequence. The ATG codon encodes the amino acid methionine. Prokaryotic polypeptides are normally processed in vivo to remove the methionine but cells transformed to express eukaryotic polypeptides often do not have a mechanism for removing it. Thus, the N-terminal amino acid of most polypeptides, produced in prokaryotic cells, but which are of eukaryotic origin, is methionine. DNA sequences with no changes to the translatable region of the sequence of a polypeptide beyond adding the requisite ATG codon, will produce polypeptide derivatives of the formula methionine-polypeptide. The present invention provides for the insertion of a single intervening amino acid, by genetic engineering methods, between the N-terminal methionine and a polypeptide product of interest, to generate the polypeptide derivative methionine-X-R described previously. This simple change results in significant and unexpected increases in expression levels of polypeptide products of interest. These amino acids so introduced are hereinafter termed "inserted amino acids". The nucleotide sequences coding for these inserted amino acids are termed "inserted codons".

The utility of the present invention was demonstrated by construction of a series of expression plasmids wherein various codons, inserted between the N-terminal methionine codon and the coding sequence for insulin-like growth factor I (IGF-I), insulin-like growth factor II (IGF-II), or proinsulin, were evaluated for their effect upon expression levels in *E. coli*. The effects, reported in the examples below, illustrate the significant and unexpected increases in expression levels of polypeptide derivatives which accompanied the insertion of certain amino acids.

Figure 1:
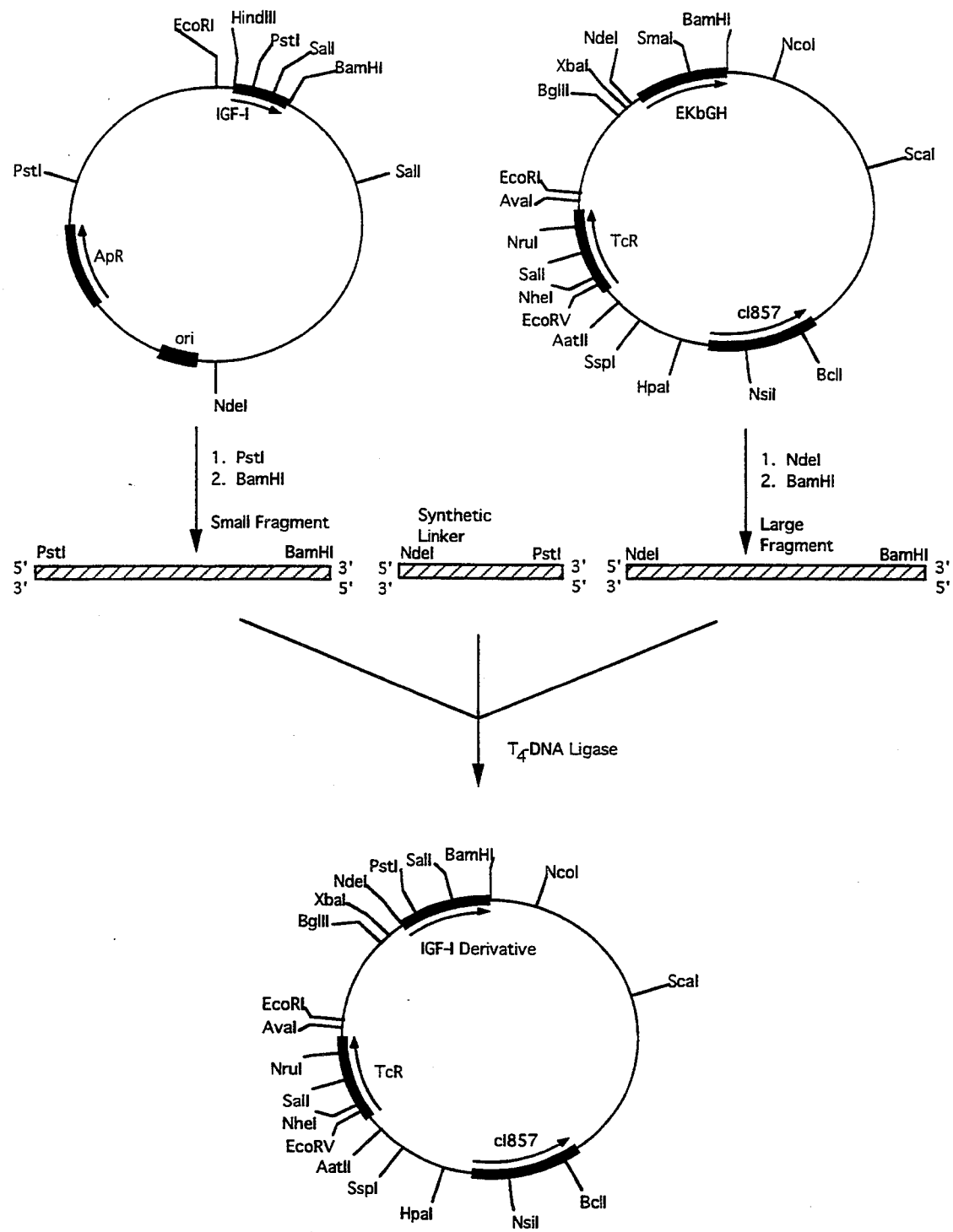
FIG. 1 synthesis is a flow diagram for the three-piece ligation of expression plasmids for IGF-I derivatives.

The general scheme for construction of recombinant DNA vectors necessary for practice of the current invention is set forth below and can be exemplified by the construction of the expression plasmids that were used to generate the data of Table 1. Table 1 reports the effect of each inserted codon upon the expression level of the resulting IGF-I derivative as a percent of the total protein expressed. These specific plasmids were constructed by a three-piece ligation as shown in FIG. 1. The IGF-I fragment from restriction sites PstI to BamHI was derived from plasmid pJE 160.3.4; the vector fragment from NdeI to BamHI was derived from plasmid pCZR126S; and the oligonucleotide linkers were chemically synthesized to complete the portion of IGF-I sequence not preserved in the first fragment and to introduce the inserted codons of interest. Thus, each expression plasmid of Table 1 carried a lambda $P_L$ promoter, the CI857 temperature sensitive repressor gene, a tetracycline resistance marker gene (TcR), the IGF-I gene plus an inserted codon, and a two cistron expression system. The double-stranded oligonucleotide linkers were formed by annealing SEQ ID NO:1 and SEQ ID NO:2 and are represented by the general formula:

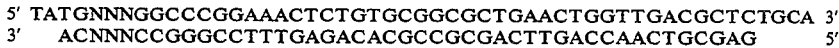

wherein NNN of the upper strand represents the triplet of nucleotides which was varied to generate the inserted codons of interest and NNN of the lower strand represents the triplet complementary to NNN of the upper strand. The linkers contain an NdeI restriction site at the 5' end and a PstI site at the 3' end. This configuration allows for conservation of the IGF-I coding sequence, including the inserted codon, upon its ligation to the pJE 160.3.4 PstI-BamHI fragment and the pCZR126S NdeI-BamHI vector fragment. Thus, the final expression plasmids vary only in the codon which appears directly 3' to the N-terminal methionyl codon of the IGF-I sequence. The synthetic linker sequences were constructed by use of the 380B DNA Synthesizer (Applied BioSystems, 850 Lincoln Drive, Foster City, Calif. 94404) using β-cyanoethyl phosphoramidite chemistry but may also be made in accordance with the methods of phosphite triester synthesis (Caruthers, M. H., Science 230, 281–285 (1985)).

Figure 2:
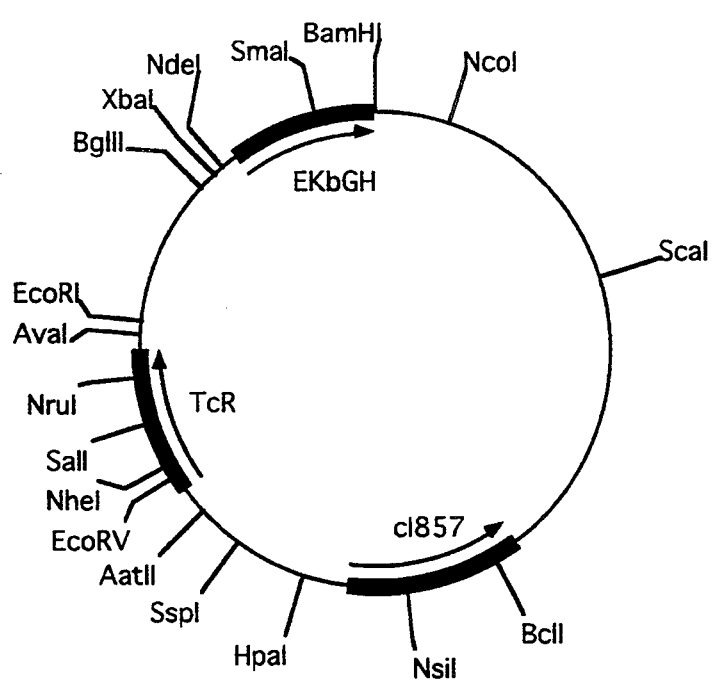
FIG. 2 is a restriction site and function map of plasmid pCZR111.
Figure 3:
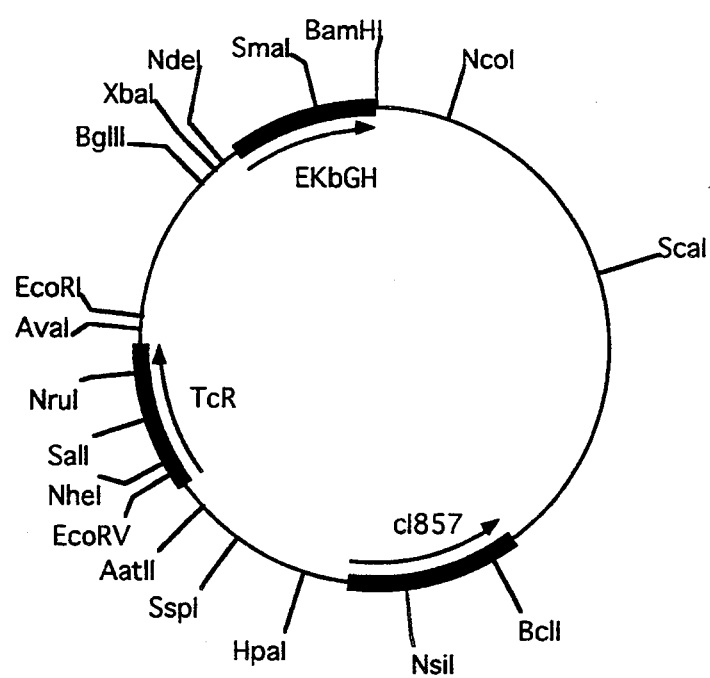
FIG. 3 is a restriction site and function map of plasmid pCZR126S.

Plasmid pCZR126S was the parental plasmid used for constructing the IGF-I expression plasmids of the present invention. Plasmid pCZR126S, as described in Example 2, was derived from plasmid pCZR111. Plasmid pCZR111 has been deposited in the Northern Regional Research Laboratory (NRRL), Peoria, Ill. 61604, and is publicly available under the accession number NRRL B-18249. Restriction site and function maps of plasmids pCZR111 and pCZR126S are provided in FIGS. 2 and 3, respectively. Plasmid pCZR126S contains a lambda PL promoter, an E. coli lipoprotein (lpp) ribosome binding site (rbs), and a tetracycline resistance gene. Plasmid pCZR126S also contains a "first-cistron" (SEQ ID NO:3) which is 5' to the IGF-I coding region. Although not a requirement of the invention, the presence of the first-cistron improves translation rates of sequences 3' to the first-cistron and is therefore a preferred construction.

Once constructed, the IGF-I expression plasmids were used to transform E. coli K12 RV308 or E. coli K12 L201 cells (NRRL B-15624 and NRRL B-18854, respectively). The cells were then grown under conditions promoting the expression of the IGF-I derivative.

Some inserted codons exhibited a differential ability to increase expression levels in one E. coli strain as compared to another strain. This effect is illustrated by the insertion of alanine which resulted in IGF-I derivative expression levels of 8.3 and 25.3 percent of total protein expressed in strains RV308 and L201, respectively.

Other inserted codons increased expression levels nearly the same in the two strains. For example, phenylalanine insertion increased IGF-I derivative expression to 18.9 and 23.1 percent in RV308 and L201, respectively.

Thus, for increasing expression levels of polypeptide products of interest in prokaryotic host cells Ala, Arg, Glu, Gly, Ile, Leu, Lys, Met, Phe, Ser, Thr, Trp, and Val are useful; while Arg, Gly, Lys, Met, Phe, Ser, Thr, and Trp are preferred; and Arg, Lys, Ser, and Thr are more preferred.

The low molecular weight polypeptides expressed as derivatives are not limited to the IGF-I protein. Other low molecular weight polypeptides, ranging from about 10 to about 100 amino acids, such as human proinsulin, human insulin A chain, human insulin B chain, human insulin-like growth factor II (IGF-II), growth hormone releasing factor (GRF), and somatostatin may also be made by exercise of the present invention. Just as the IGF-I gene, oligonucleotide, and parental plasmid were ligated to allow generation of the many IGF-I derivatives, coding sequences for other desired proteins may be employed in substantial accordance with the present teachings to generate other derivatives within the scope of the present invention.

In addition, skilled artisans realize that the degeneracy of the genetic code allows variance from the inserted codons actually synthesized and characterized in Table 1 without changing the amino acid encoded; that is, an amino acid can be encoded by more than one codon. These alternative codons are contemplated by and are included within the scope of the present invention.

The present invention is not limited to the use of plasmid pCZR126S. Any plasmid containing or designed to contain the appropriate promoter, not just lambda PL, but promoters like trp, lpp, and tac, may also be used. Such vectors include but are not limited to pBR322. Just as the present invention is not limited to any particular plasmid or protein encoding gene, the transformed host cell is not limited to either E. coli K12 RV308 or E. coli K12 L201. Any host cell that will allow expression of the desired gene may be used. Therefore, E. coli MM294, E. coli JM101, E. coli W3110, E. coli C600, E. coli WA704, Bacillus, Streptomyces, and yeast, for example, may also be used for purposes of the present invention.

Several procedures well known in the art may be used to generate the desired extra amino acid sequence at the N-terminus of a given protein. Such procedures include producing such derivatives by classical solution phase, solid phase, or by recombinant DNA methodology.

IGF-I derivatives and other polypeptide derivatives have the potential to elicit undesirable immunological reactions when used in humans and other mammals. These reactions are believed to be caused by the extra amino acid sequences that are not present in the natural protein. In effect, the non-natural amino acid sequences are believed to be recognized in vivo as foreign substances. Therefore, in order to eliminate potential immunological responses that the extra amino acid sequences might elicit, it is desirable to cleave the extra amino acid sequences from the protein. Several cleavage methods, chemical or enzymatic, are well known in the art and may be employed to remove the extra amino acid sequences to generate non-immunogenic, native protein. Chemical agents useful for cleaving proteins are cyanogen bromide, 2-(2-nitrophenyl-sulfenyl)-3-bromo-3′-methylindolinium (BNPS-akatole), hydroxylamine, and the like. Cyanogen bromide cleaves polypeptides at the C-terminus of a methionine residue. Therefore, the selective cleavage site is a methionine residue itself. Hydroxylamine cleaves at the C-terminus of the moiety -Asn-Z- in which Z is Gly, Leu, or Ala. BNPS-akatole cleaves at the C-terminus of a tryptophan residue.

Examples of enzymatic agents useful for cleavage are trypsin, papain, pepsin, plasmin, thrombin, enterokinase, and the like. Each effects cleavage at a particular amino acid sequence which it recognizes. Enterokinase, for example, recognizes the amino acid sequence -(Asp)$_n$-Lys- in which n is an integer from 2 to 4.

Edman degradation is another cleavage method which sequentially removes single N-terminal amino acids from the polypeptide.

The following preparations and examples further illustrate and detail the invention disclosed herein but are in no way intended to limit the scope of the invention. Enzymes referred to in the examples are available unless otherwise indicated from Bethesda Research Laboratories (BRL), Gaithersburg, Md. 20877, New England Biolabs Inc. (NEB), Beverly, Mass. 01915, or Boehringer Mannheim Biochemicals (BMB), 7941 Castleway Drive, Indianapolis, Ind. 46250 and are used in substantial accordance with the manufacturer's recommendations. Many of the techniques employed herein are well known to the artisan of ordinary skill. Molecular biology techniques are described in detail in laboratory manuals such as *Molecular Cloning, A Laboratory Manual* (1982) edited by Maniatis, T. et al. and *Current Protocols in Molecular Biology*, (1987) edited by Ausubel et al. The skilled artisan will recognize that alternate procedures can be substituted for various procedures presented below.

EXAMPLE 1

Isolation of Plasmid pCZR111

Lyophils of *E. coli* K12 RV308/pCZR111 are decanted into tubes containing 10 ml TY medium (2% tryptone, 0.06% yeast extract, 10 mMNaCl, 2.5 mM KCl, 10 mM each of MgCl$_2$ and MgSO$_4$, 20 ELM glucose, in deionized water (pH 7.0)) and incubated two hours at 32° C., at which time the cultures are made 5 μg/ml in tetracycline and then incubated at 32° C. overnight. The *E. coli* K12 RV308/pCZR111 cells are cultured at 32° C., because the cells comprise a temperature-sensitive cI repressor gene integrated into the plasmid DNA. When cells that comprise a wild-type lambda P$_L$ repressor gene or do not comprise a lambda P$_L$ promoter are utilized in this plasmid isolation procedure, as described in subsequent examples herein, the temperature of incubation is 37° C.

A small portion of the overnight culture is placed on TY-agar (TY medium with 15 g/l agar) plates containing 5 μg/ml tetracycline in a manner so as to obtain a single colony isolate of *E. coli* K12 RV308/pCZR111. The single colony obtained is inoculated into 10 ml of TY medium containing 5 μg/ml tetracycline and incubated overnight at 32° C. with vigorous shaking. The 10 ml overnight culture is inoculated into 500 ml TY medium containing 5 μg/ml tetracycline and incubated at 32° C. with vigorous shaking until the culture reaches stationary phase.

The cells are harvested by centrifugation at 4000X g for 10 minutes at 4° C., and the supernatant is discarded. The cell pellet is washed in 100 ml of ice-cold STE buffer (0.1M NaCl; 10 mM tris[hydroxymethyl]-aminomethane hydrochloride (Tris-HCl) (pH 7.8); and 1 mM ethylenediaminetetraacetic acid (EDTA)). After washing, the cell pellet is resuspended in 10 ml of Solution 1 (50 mM glucose; 25 mM Tris-HCl (pH 8.0); and 10 mM EDTA) containing 5 mg/ml lysozyme and left at room temperature for 10 minutes. Twenty ml of Solution 2 (0.2N NaOH and 1% sodium dodecyl sulfate (SDS)) are then added to the lysozyme-treated cells, and the solution is gently mixed by inversion. The mixture is incubated on ice for 10 minutes.

Fifteen ml of ice-cold 5M potassium acetate (pH 4.8) are added to the lysed-cell mixture and the solution mixed by inversion. The solution is incubated on ice for 10 minutes. The 5M Potassium acetate solution is prepared by adding 11.5 ml of glacial acetic acid to 28.5 ml of water and 60 ml of 5M Potassium acetate; the resulting solution is 3M with respect to potassium and 5M with respect to acetate.

The lysed cell mixture is centrifuged in a Beckman SW27 (or its equivalent) at 20,000 rpm for 20 minutes at 4° C. The cell DNA and debris form a pellet on the bottom of the tube. About 36 ml of supernatant are recovered and 0.6 volumes of isopropanol are added. The resulting solution is mixed and left at room temperature for 15 minutes. The plasmid DNA is collected by centrifugation at 12,000X g for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer (10 mM Tris-HCl (pH 8.0) and 1 mM EDTA).

Eight grams of CsCl are added to the DNA solution. About 0.8 ml of a 10 mg/ml solution of ethidium bromide in water are added for each 10 ml of CsCl-DNA solution. The final density of the solution is about 1.55 g/ml and the ethidium bromide concentration is about 600 μg/ml. The solution is transferred to a Beckman Type 50 centrifuge tube, filled to the top with paraffin oil, sealed, and centrifuged at 45,000 rpm for 24 hours at 20° C. After centrifugation, two bands of DNA are visible in ordinary light. After removing the cap from the tube, the lower DNA band is removed by using a syringe with a 21 gauge hypodermic needle inserted through the side of the centrifuge tube.

The ethidiumbromide is removed by several extractions with water-saturated 1-butanol. The CsCl is removed by dialysis against TE buffer. After extractions with buffered phenol and then chloroform, the DNA was precipitated, washed with 70% ethanol, and dried.

About 1 mg of plasmid pCZR111 is obtained and stored at 4° C. in water at a concentration of about 0.1 μg/μl.

EXAMPLE 2

Construction of Plasmid pCZR126S

About 50 μl of 10X XbaI buffer (600 mM Tris-HCl, 100 mM MgCl$_2$, 1M NaCl, and 10 mM 2-mercaptoethanol (pH 7.5 at 37° C.)), 15 μl (150 units) of XbaI restriction enzyme, and 185 μl of water were added to 250 μl of water containing about 25 μg of plasmid pCZR111. The digestion proceeded at 37° C. for 1 hour. XbaI digested pCZR111 was then extracted in phenol, 1/10 volume 3M sodium acetate was added, and 3 volumes of ethanol were added. The mixture was incubated in a dry ice-ethanol bath for 5 minutes and then centrifuged. The precipitated DNA was resuspended in 50 μl water.

The XbaI digested plasmid pCZR111 was digested with BamHI as follows. About 0.2 μl (2 units) of BamHI restriction enzyme, 10 μl of 10X BamHI buffer (100 mM Tris-HCl, 50 mM MgCl$_2$, 1M NaCl, and 10 mM 2-mercaptoethanol (pH 8.0 at 37° C.)), and 90 μl of water were added to the 50 μl of XbaI digested pCZR111 obtained hereinabove. The digestion proceeded for 5 minutes at 37° C. The digested pCZR111 was extracted in phenol and 1/10 volume of sodium acetate was added followed by addition of 3 volumes of ethanol. Precipitated DNA was resuspended in 50 μl of TE buffer.

The XbaI and BamHI digested pCZR111 was then loaded onto an agarose gel and the DNA band at about 5.8 kilobases (kb) was isolated. Plasmid pCZR126S was produced by ligating the approximately 5.8 kb fragment of pCZR111 to an XbaI to NdeI linker and a synthetic gene encoding enterokinase cleavable bovine growth hormone derivative (EK-bGH), which contained an NdeI site on its 5' end and a BamHI site on its 3' end.

The XbaI to NdeI linker was formed from two single-stranded oligonucleotides (SEQ ID NO:4 AND SEQ ID NO:5) which were synthesized on a 380B DNA Synthesizer. Following purification by polyacrylamide gel electrophoresis, equal-molar amounts of the single-stranded oligonucleotides were annealed and phosphorylated according to the teachings of Brown, E. L., Belagaje, R., Ryan, M. J., and Khorans, H. G. (1979) *Methods in Enzymology*, Ed. by Wu, R., Academic Press, N.Y. 68, 109–151 to form the following double-stranded sequence:

```
5' CTAGAGGGTATTAATAATGTATATTGATTTTAATAAGGAGGAATAATCA   3'
3'     TCCCATAATTATTACATATAACTAAAATTATTCCTCCTTATTAGTAT  5'
```

The gene encoding EK-bGH was constructed from 16 chemically synthesized pieces of single-stranded DNA, ranging from 71 to 83 nucleotides long, which together comprise both complementary strands of the entire gene (SEQ ID NO:6 and SEQ ID NO:7). The oligonucleotides were synthesized on a 380B DNA Synthesizer and annealed and phosphorylated as described above and ligated with T$_4$-DNA ligase to form the final sequence.

Construction of plasmid pCZR126S was accomplished by ligation of the following site components: about 0.28 μg of the 5.8 kb fragment obtained from plasmid pCZR111 after complete digestion with XbaI and partial digestion with BamHI in a total volume of 2 μl; about 0.18 μg of the synthetic gene encoding a bovine growth factor derivative which has a 5' terminus corresponding to an XbaI site and a 3' terminus corresponding to a BamHI site in a total volume of 2.5 μl; and 8.75 picomoles (pmoles) of the chemically synthesized XbaI to NdeI linker in 1 μl. The plasmid components were added to 6 μl of 5X ligation buffer (250 mM Tris-HCl (pH 7.6), 50 mM MgCl$_2$, 5 mM adenosinetriphosphate (ATP), 5 mM dithiothreitol (DTT), 25% v/v polyethylene glycol 8,000), 2 μl of T$_4$-DNA ligase, and 16.5 μl of water. The ligation mixture was incubated overnight at 16° C. The circularized plasmid pCZR126S was then used to transform *E. coli* RV308 cells in substantial accord with the method of Example 3B4 and plasmid pCZR126S was isolated in substantial accord with Example 1.

EXAMPLE 3

Expression of Met-Arg-IGF-I

A. Construction of plasmid pJE 160.3.4

1. Isolation of HindIII-BamHI Vector Fragment of pBR322

About 10 μg of plasmid pBR322 (commercially available from BRL) was suspended in 20 μl of 10X HindIII buffer (500 mM NaCl, 500 mM Tris-HCl (pH 8.0), 100 mM MgCl$_2$ 1 mg/ml bovine serum albumin (BSA)), 2 μl (20 units) of HindIII restriction enzyme and 170 μl of water. The components were gently mixed and incubated at 37° C. for 2 hours. An aliquot of this reaction mixture was checked for complete conversion of the plasmid DNA to linearized DNA on a 1% agarose gel. To the rest of the reaction mixture was then added 20 μl of 0.3M sodium acetate and 1 ml of ethanol. The mixture was gently mixed and kept at −70° C. for 2 hours. The precipitated DNA was collected by centrifugation, washed once with 1 ml of 75% ethanol, and the pellet was dried in vacuo for about 30 minutes.

The pellet was redissolved in 20 μl of buffer (1.5M NaCl, 60 mM Tris-HCl (pH 7.9), 60 mM MgCl$_2$, 1 mg/ml BSA) and 180 μl of water. 2 μl (20 units) of the BamHI restriction enzyme was added and the solution was gently mixed and incubated at 37° C. for 2 hours. The DNA was precipitated with 1 ml of ethanol and 20 μl of 0.3M sodium acetate and electrophoresed on a 1% low melting agarose gel. The large HindIII-BamHI restriction fragment was sliced from the gel and the DNA was recovered by passing through an Elutip-d column using the procedure as recommended by the vendor (Schleicher and Schull, Keene, N.H. 03431). After precipitation and drying, the DNA was stored in 30 μl of 10 mM Tris-HCl (pH 8.0).

2. Synthesis of IGF-I Gene

Figure 4:
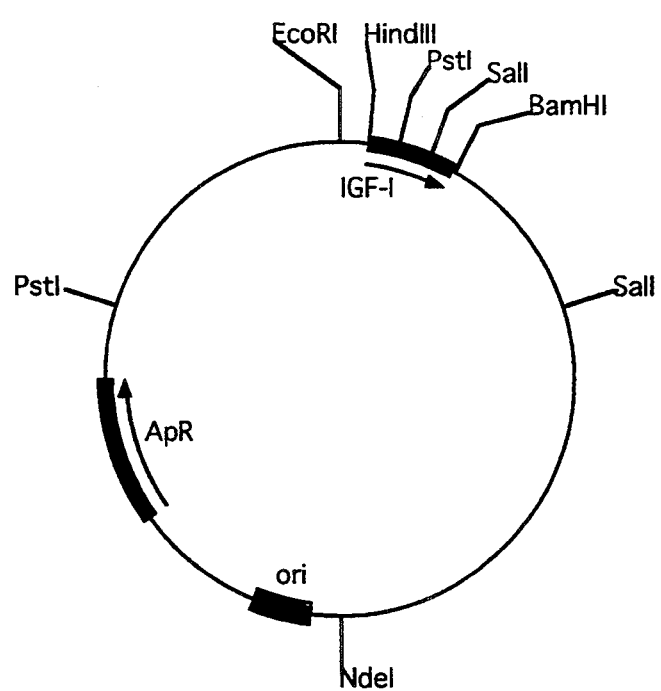
FIG. 4 is a restriction site and function map of plasmid pJE160.3.4.

The coding region of IGF-I gene (SEQ ID NO:8 and SEQ ID NO:9) was synthesized using codons commonly found in highly expressed *E. coli* genes and designed to include convenient restriction sites for cloning purposes as shown in FIG. 4. The HindIII to SalI fragment contains enterokinase cleavage sequences coding for amino acids-(Asp)$_4$-Lys- and coding sequences for amino acids 1 to 44 of IGF-I whereas the SalI to BamHI fragment contains coding sequences for amino acids 45 to 70 of IGF-I respectively. Two stop codons TAA and TAG were added at the 3'-end of the latter half of the gene fragment to provide a site for termination of translation. The total synthesis of this gene involved chemical synthesis and enzymatic joinings of 38 oligonucleotides, varying in size from decamer to heptadecamer, by the improved phosphotriester method of Narang, S. A., Hsiung, H. and Brousseau, R. (1980), *Methods in Enzymology* 68, 90–98. A variety of DNA synthesizing instruments which are now commercially available and well known may also be used to synthesize much larger fragments for assembly of the final sequence.

After purifying each oligonucleotide by polyacrylamide gel electrophoresis or reversed high pressure liquid chromatography, the oligonucleotides were phosphorylated according to the teachings of Brown, E. L., in order to facilitate the ligation and construction of two IGF-I-encoding DNA fragments. One fragment contained a HindIII restriction site at the 5' end and a SalI site at the 3' end. The second fragment contained a SalI restriction site at the 5' end and a BamHI site at the 3' end.

3. Ligation

5 μl of the HindIII and BamHI digested plasmid pBR322 was mixed with 5 pmoles each of the HindIII-SalI and SalI-BamHI IGF-I-encoding fragments generated above in a buffer (50 μl) containing 50 mM Tris-HCl (pH 7.6), 10 mM MgCl$_2$, 10 mM DTT, 800 μM ATP, and 3.5 units of T$_4$-DNA ligase. The reaction was incubated at 4° C. overnight and the resulting plasmid, designated pJE 160.3.4, was transformed into *E. coli* K12 RV308 as follows. A restriction site map of pJE 160.3.4 is shown in FIG. 4.

4. Preparation of Frozen, Competent *E. coli* K12 RV308 cells.

5 ml portion of TY medium was inoculated with *E. coli* K12 RV308 and the resulting culture incubated at 37° C. overnight with shaking. The overnight cultures were diluted with TY medium containing 10 mM MgSO$_4$ and 10 mM MgCl$_2$ to a final volume of 250 ml, and then incubation at 37° C. was continued until the OD$_{550}$ reached 0.5–0.6 absorbance units. The cells were then collected by centrifugation, washed with 125 ml of chilled 10 mM NaCl and again collected by centrifugation. The cell pellets were resuspended in 125 ml of 30 mM CaCl$_2$ and the resulting suspension was incubated on ice for 20 to 30 minutes. The cells were then collected by centrifugation and the resulting pellets were resuspended in 12.5 ml of a cold solution of 15% glycerol in 30 mM CaCl$_2$ and 10 mM Tris-HCl (pH 8.0). The cell suspension was then aliquoted in 0.2 ml portions into prechilled tubes which were immediately placed and stored at −70° C. The cells prepared by this procedure remain viable and competent for transformation for up to one year.

5. Transformation

One of the tubes containing the competent *E. coli* K12 RV308 cells was removed from storage at −70° C., thawed, and mixed with the ligated DNA from part A3 above. The cell DNA mixture was incubated on ice for one hour, heat shocked at 37° C. for 45 seconds, and then chilled on ice for about 2 minutes. The cell-DNA mixture was diluted into 5 ml with TY medium and incubated at 30° C. for about 1 hour. 200 μl aliquots were plated on TY-agar plates containing 50 μg/ml ampicillin and the plates were placed in an incubator at 37° C. until colonies appeared.

Colonies were picked from these plates and cultures grown at 32° C. overnight in 3 ml of TY medium containing 100 μg/ml ampicillin. Plasmids were isolated from the cultures by the rapid alkaline extraction procedure described in *Molecular Cloning*, pp. 368–369. The presence of the correct IGF-I gene fragment (239 bp) was determined by HindIII-BamHI restriction analysis of the plasmids and the desired plasmid pJE 160.3.4 was further identified by sequence analysis.

6. Isolation of PstI-BamHI Restriction fragment from pJE 160.3.4

About 50 μg of plasmid pJE 160.3.4 was resuspended in 30 μl of 10X PstI buffer (1M NaCl, 100 mM Tris-HCl (pH 7.5)), 100 mM MgCl$_2$, 1 mg/ml BSA), 5 μl (100 units) of PstI restriction enzyme and 215 μl of water. The solution was gently mixed and incubated at 37° C. for 2 hours. 4 μl (100 units) of BamHI restriction enzyme was then added to this reaction mixture and the incubation at 37° C. was continued for another 2 hours. The DNA was precipitated with three volumes of ethanol and 0.3M sodium acetate and electrophoresed on a 1% low melting agarose gel. The smaller PstI-BamHI restriction fragment was sliced from the gel and the DNA was recovered by passing through an Elutip-d column. After precipitation and drying, the DNA was stored in 30 μl of 10 mM Tris-HCl (pH 8.0).

B. Construction of pRB5.77A1

1. Isolation of NdeI-BamHI Vector Fragment

About 16 μl (20 μg) of plasmid pCZR126S was mixed with about 20 μl 10X NdeI buffer (500 mM Tris-HCl (pH 7.5), 100 mM MgCl$_2$, 1M NaCl, 10 mM, 20 μl 1 mg/ml BSA, 45 μl 0.3M 2-mercaptoethanol), 140 μl water, and 4 μl (40 units) NdeI restriction enzyme. The mixture was incubated at 37° C. for 2 hours. The DNA was precipitated with 1 ml ethanol and 20 μl sodium acetate.

After centrifugation and drying, the pellet was dissolved in 20 μl 10X BamHI buffer. About 20 μl 1 mg/ml BSA, 160 μl water, and 4 μl (40 units) BamHI were added. The mixture was incubated at 37° C. for 2 hours. The DNA was again precipitated with 1 ml ethanol and 20 μl 3M sodium acetate and electrophoresed on a 1% low melting agarose gel. The larger NdeI-BamHI restriction fragment was sliced from the gel and the DNA was recovered by melting the agarose and passing through an Elutip-d column. After precipitation and drying, the DNA was stored in 40 μl Tris-HCl buffer (pH 7.6).

2. Synthesis of Oligonucleotide Linkers

Two oligonucleotides (SEQ ID NO:10 and SEQ ID NO:11) were prepared on a 380B DNA Synthesizer to form the following linker having an NdeI restriction site at the 5' end and a PstI site at the 3' end:

```
5' TATGCGTGGCCCGGAAACTCTGTGCGGCGCTGAACTGGTTGACGCTCTGCA 3'
3'     ACGCACCGGGCCTTTGAGACACGCCGCGACTTGACCAACTGCAG     5'
```

3. Ligation

Figure 5:
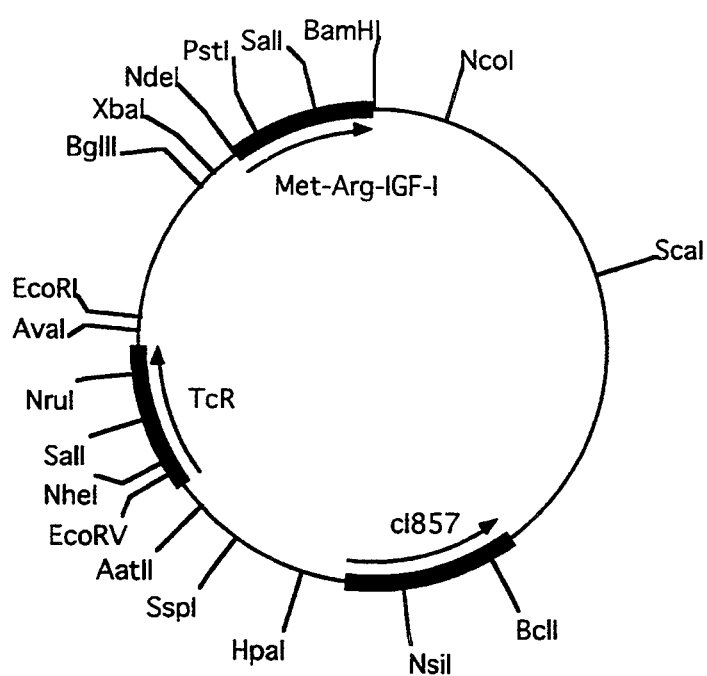
FIG. 5 is a restriction site and function map of plasmid pRB577A1.

About 2.5 μl (10 pmoles) of the oligonucleotide linker synthesized in part B2, 3 μl (0.25 pmoles) of the vector fragment produced in part B1, and 7.5 μl (10 pmoles) of the IGF-I fragment isolated in part A6 were mixed with 5 μl of 10X Ligase Buffer (500 mM Tris-HCl (pH 7.6), 100 nM MgCl$_2$), 3 μl 10 mM ATP, 0.5 μl 1M DTT, 28.5

μl water, and 2.5 units T4-DNA ligase. The mixture was incubated overnight at 4° C. About 50 μl 10 mM Tris-HCl (pH 7.6) and 3 μl 1M CaCl2 were added to the mixture. The resultant plasmid was designated pRB5.77A1 and is shown in FIG. 5.

4. Transformation

About 50 μl of the ligation mixture from part B3 was used to transform 150 μl of frozen competent E. coli K12 RV308 cells. The ligation mixture was mixed with the cells and incubated on ice for one hour, heat-shocked at 37° C. for 45 seconds, then chilled on ice for about 2 minutes. The cell-DNA mixture was diluted into 1 ml of TY medium and incubated at 32° C. for one hour. About 100 μl aliquots were plated on TY-agar plates containing 5 μg/ml tetracycline until colonies appeared. The desired transformants were identified by restriction site and sequence analysis of the plasmid DNA. Colonies were picked from the plates and cultures grown at 30° C. overnight in 3 ml TY medium containing 5 μg/ml tetracycline. 50 μl of the overnight cultures were inoculated into 2.5 μl TY medium containing 5 μg/ml tetracycline and grown for 1 hour at 30° C. The temperature was then shifted to 42° C. for 3 hours. Raising the temperature to 42° C. induced the lambda $P_L$ promoter, thus, resulting in high level expression of the desired Met-Arg-IGF-I derivative.

1 μl of the culture was pelleted and the pellet was dissolved in Sample Buffer (0.125M Tris-HCl (pH 6.8), 1M 2-mercaptoethanol, 2% SDS, 30% glycerol, 6M urea) to obtain $OD_{550}$ of 0.02.

This solution was then electrophoresed on 15% SDS polyacrylamide gel. Polypeptide bands were visualized by staining with Coomassie Brilliant Blue. A scanning gel densitometer was used to assess expression levels of the desired polypeptide. Plasmid pRB577A1, transformed into E. coli K12 RV308 cells to produce E. coli strain K12 RV308/pRB577A1, caused expression of Met-Arg-IGF-I as 22% of the total protein expressed by the cells as shown in Table 1.

Additional plasmids, coding for IGF-I derivatives of the formula Met-X-IGF-I, were constructed in substantial accordance with this example, except that the linker sequence prepared in part B2 above was replaced with the linker sequence:

formed from SEQ ID NO:1 and SEQ ID NO:2 wherein NNN was the "Inserted Codon" of Table 1. In each instance, 0.25 pmoles of NdeI-BamHI digested DNA fragment of Example 3B1; 10 pmoles of PstI-BamHI IGF-I fragment from Example 3A6; and 10 pmoles of the NdeI-PstI linker from Example 3B2 were ligated as described in Example 3B3 to form the expression vector. Transformation into E. coli K12 RV308 or E. coli K12 L201 was performed as described in Example 3B4. Table 1 reports the effect of each inserted codon upon the expression level of the resulting IGF-I derivative as a percent of the total protein expressed by each of the strains of E. coli and includes the expression level of Met-IGF-I as a comparative standard.

TABLE 1

| | Met-X-IGF-I CONSTRUCTIONS | | | | | |
|---|---|---|---|---|---|---|
| EXAMPLE NO. | DERIVATIVE | INSERTED CODON | STRAINS | | EXPRESSION (%) | |
| | | | RV308 | L201 | RV308 | L201 |
| 3-4 | Met-ARG-IGF-I | CGT | RB577A1 | RB581A | 22.0 | 29.4 |
| 5-6 | Met-ALA-IGF-I | GCT | RB5102E2 | RB5137E2 | 8.3 | 25.3 |
| 7-8 | Met-GLU-IGF-I | GAA | RES106G1 | RB5127G1 | 9.6 | 25.2 |
| 9-10 | Met-GLY-IGF-I | GGT | RB5106E4 | RB5137E4 | 15.3 | 25.3 |
| 11-12 | Met-ILE-IGF-I | ATC | RB5106H1 | RB5137H1 | 12.7 | 22.7 |
| 13-14 | Met-LEU-IGF-I | CTG | RB5106D7 | RB5137D7 | 14.4 | 20.8 |
| 15-16 | Met-LYS-IGF-I | AAA | RB5106F8 | RB5137F8 | 19.8 | 29.3 |
| 17-18 | Met-Met-IGF-I | ATG | RB5l06H9 | RB5137H9 | 17.6 | 24.1 |
| 19-20 | Met-PHE-IGF-I | TTC | RB5106C6 | RB5137C6 | 19.9 | 23.1 |
| 21-22 | Met-SER-IGF-I | TCT | RB5106B2 | RB5137B2 | 19.9 | 28.5 |
| 23-24 | Met-THR-IGF-I | ACT | RB5106B4 | RB5137B4 | 20.0 | 27.8 |
| 25-26 | Met-TRP-IGF-I | TGG | RB5106A1 | RB5127A1 | 18.1 | 26.0 |
| 27-28 | Met-VAL-IGF-I | GTT | RE5106E1 | RB5127E1 | 5.0 | 21.9 |
| Control | Met-IGF-I | None | | | ND | ND |

ND = Not Detectable

EXAMPLE 29

Expression of Met-Arg-Proinsulin

A. Construction of Plasmid DRB145

An analog of the native human proinsulin gene (hpI) (SEQ ID NO:12 and SEQ ID NO:13) was first custom synthesized and cloned into pUCL8 plasmid (commercially available from BRL). The gene was synthesized using an automated 380B DNA Synthesizer as described in Example 2.

One of the clones having the correct sequence was selected for the production of cesium chloride purified DNA. The plasmid was isolated in substantial accordance with Example 1. About 6 μl (20 μg) of this plasmid DNA was added to 20 μl of buffer (150 mM NaCl, 10 mM Tris-HCl (pH 7.8), 6 mM MgCl2, 6 mM 2-mercaptoethanol, 100 μg/ml BSA), 5 μl (40 units) NdeI restriction enzyme and 169 μl water. After mixing, the reaction was incubated at 37° C. for 2 hours. The DNA was precipitated by adding sodium acetate to a final concentration of 0.3M, adding three volumes of ethanol, mixing and chilling to −70° C., and centrifuging. The DNA pellet was washed with 70% ethanol (1 ml); dried; and dissolved in 20 μl of buffer (150 mm NaCl, 6 mM Tris-HCl (pH 7.9), 6 mM MgCl2, 100 μg/ml BSA), 2 μl (40 units) of BamHI restriction enzyme, and 178 μl water. After gentle mixing, the reaction was incubated at 37° C. for 2 hours. The DNA was again precipitated with three volumes of ethanol as above and electrophoresed on a 1% low melting agarose gel. The desired 5' TATGNNNGGCCCGGAAACTCTGTGCGGCGCTGAACTGGTTGACGCTCTGCA 3'
3'     ACNNNCCGGGCCTTTGAGACACGCCGCGACTTGACCAACTGCGAG DNA fragment corresponding to about 270 bp was sliced from the gel and then DNA was recovered by melting the agarose and passing through an Elutip-d column. After precipitation and drying, the purified hpI DNA was stored in 30 μl of 10 mM Tris-HCl 8.0).

About 15 μg of plasmid pCZR126S (from Example 2) was suspended in 20 μl of 10X NdeI buffer. 5 μl (40 units) of NdeI restriction enzyme and 175 μl water were added, and the mixture was gently mixed and incubated at 37° C. for 2 hours. After the incubation, the DNA was precipitated with three volumes of ethanol as above; dried; and then resuspended in 20 μl of 10X BamHI buffer, 2 μl (40 units) of BamHI restriction enzyme, and 178 μl water. After gentle mixing, the reaction mixture was incubated at 37° C. for 2 hours. The DNA was again precipitated with three volumes of ethanol and electrophoresed on a 1% low-melting agarose gel. The larger fragment, corresponding to the NdeI-BamHI vector DNA fragment, was sliced from this gel and the DNA was recovered by the Elutip-d column procedure. After precipitation and drying, the vector DNA was stored in 35 μl of 10 mM Tris-HCl (pH 8.0).

About 2.5 μl of the NdeI-BamHI vector DNA fragment of pCZR126S was mixed with 12 μl of the purified hpI gene fragment from above, 4 μl of 10 mM ATP, 0.5 μl of 1M DTT, 5 μl of 10X Ligase Buffer, 26 μl of water, and 0.5 μl (3–5 units) of T4-DNA ligase. The reaction mixture was incubated at 4° C. for 16 hours. The ligated mixture was diluted with 50 μl of 10 mM Tris-HCl (pH 7.6) and 3 μl of 1M CaCl2 and then subsequently transformed into E. coli K12 RV308 in substantial accordance with the teaching of Example 3B4. The cells were plated on TY-agar plates supplemented with 5 μg/ml tetracycline then incubated overnight at 32° C.

Figure 6:
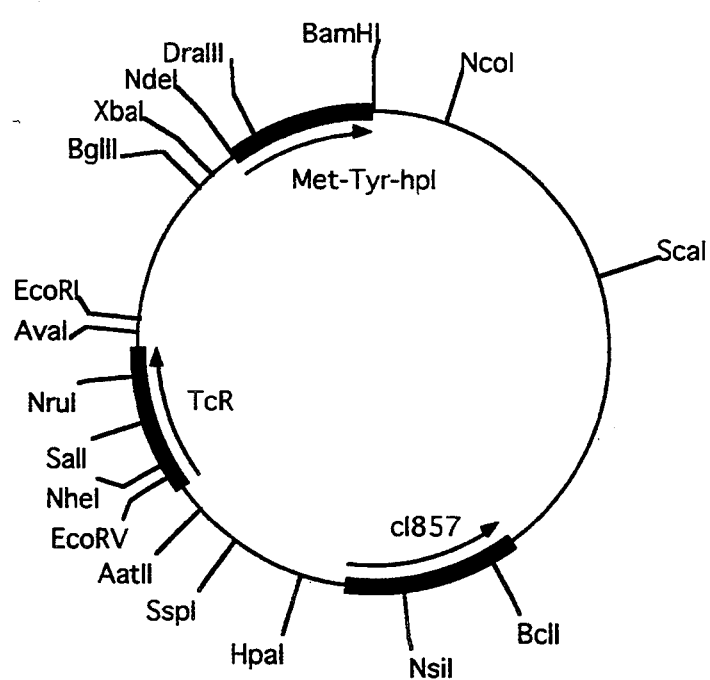
FIG. 6 is a restriction site and function map of plasmid pRB145.

Plasmids from 3 ml cultures were isolated from tetracycline resistant colonies by the rapid alkaline extraction procedure described in *Molecular Cloning*, pp. 368–369. The presence of the correct hpI gene fragment was found using polyacrylamide gel electrophoresis to analyze the XbaI-BamHI digested fragment. Those plasmids with the correct size (about 315 bp) inserts were selected for amplification and purification. The plasmid containing the hpI gene was designated pRB145. A restriction site and function map of plasmid pRB145 is presented in FIG. 6 of the accompanying drawings.

B. Construction of Plasmid pRB145B

About 10 μg of plasmid pRB145 was suspended in 20 μl of 10X DraIII buffer (500 mM Tris-HCl (pH 7.5), 1M NaCl, 100 mM MgCl2, 10 mM DTT), 4 μl (20 units) of DraIII restriction enzyme, and 176 μl of water, gently mixed and incubated at 37° C. for 2 hours. An aliquot of the reaction mixture was checked on a 1% agarose gel for complete conversion of the plasmid DNA to linearized DNA. To the rest of the reaction mixture was then added 2.5 μl (20 units) of NdeI restriction enzyme and then incubation at 37° C. was continued for another 2 hours. The DNA was precipitated with three volumes of ethanol and 0.3M sodium acetate and electrophoresed on a 1% low melting agarose gel. The larger NdeI-DraIII restriction fragment was sliced from the gel and the DNA was recovered by passing through an Elutip-d column. After precipitation and drying, the DNA was stored in 30 pl of 10 mM Tris-HCl 8.0).

The DNA linker (40 bp) corresponding to the NdeI-DraIII restriction fragment of the hpI gene was synthetically prepared. Two single-stranded oligonucleotides (SEQ ID NO:14 and SEQ ID NO:15 were prepared by an 380B DNA Synthesizer and purified by polyacrylamide gel electrophoresis. The oligonucleotides (200 pmoles) were annealed and phosphorylated according to the teachings of Brown, E. L., et al to form the following linker:

```
5'  TATGCGTTTTGTTAACCAACACCTGTGCGGCTCCCACCTG  3'
3'     ACGCAAAACAATTGGTTGTGGACACGCCGAGGGTG      5'
```

Figure 7:
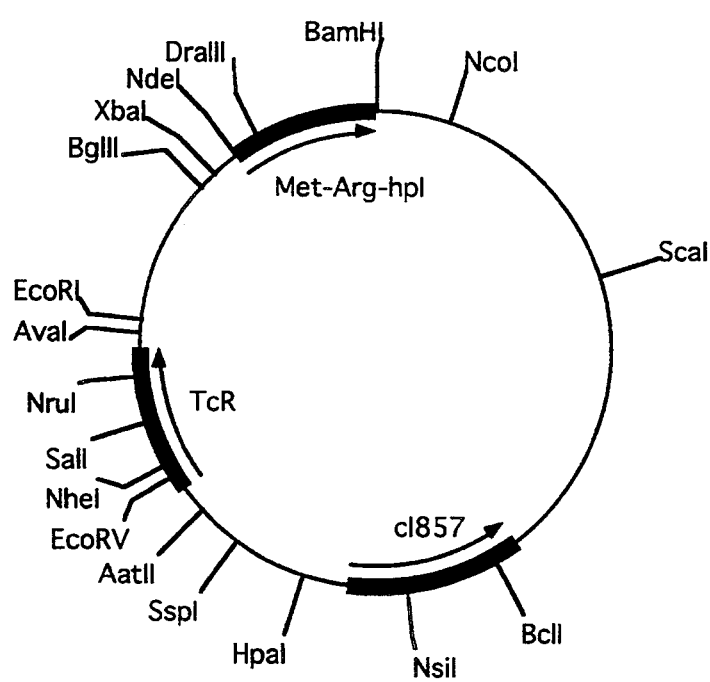
FIG. 7 is a restriction site and function map of plasmid pRB145B.

About 15 pmoles of this linker was mixed with 2.5 μl of NdeI-DraIII digested pRB145 in a buffer containing 50 mM Tris-HCl (pH 7.6), 100 mM MgCl2, 100 mM DTT, 800 μM ATP, and 3.6 units of T4-DNA ligase. The reaction mixture was incubated at 4° C. overnight and then transformed into E. coli K12 RV308 in accordance with the procedure of Example 3B4. The desired transformant, E. coli K12 RV308/pRB145B, was identified by sequence analysis of its plasmid DNA. The cells were grown and protein expression was induced and quantitated as described in Example 3B4. The expressed protein differs from Met-hpI which would normally be expressed only by the presence of the Arg inserted amino acid. Results are shown in Table 2. A restriction site and function map of plasmid pRB145B is presented in FIG. 7 of the accompanying drawings.

Example 30

Expression of Met-Arg-[Lys(28)-Pro(29)]-Proinsulin

A. Construction of Plasmid pRB164A

About 30 μg of plasmid pRB145 were suspended in 20 μl of 10X NdeI buffer and 5 μl (40 units) of NdeI restriction enzyme and 175 μl of water were added. The solution was gently mixed and incubated at 37° C. for 1 hour. About 2 μl (40 units) of BamHI restriction enzyme were then added to the reaction mixture and the incubation at 37° C. was continued for another 2 hours. The DNA was precipitated with three volumes of ethanol and 0.3M sodium acetate and electrophoresed on a 1% low melting agarose gel. The smaller (about 270 bp) NdeI-BamHI restriction fragment encoding the hpI gene was sliced from the gel and the DNA was recovered by passing through an Elutip-d column. After precipitation and drying, the DNA was stored in 30 μl of 10 mM Tris-HCl (pH 8.0).

To this DNA (30 μl) was then added 20 μl of 10X AvaII buffer (50 mM NaCl, 6 mM Tris-HCl (pH 8.0), 10 mM units) of AvaII restriction enzyme, and 175 μl of water. After gently mixing, this reaction mixture was incubated at 37° C. for 2 hours. The DNA was precipitated with three volumes of ethanol and 3M sodium acetate (20 μl) and then electrophoresed on a 1.2% low melting agarose gel. The larger AvaII-BamHI restriction fragment (about 156 bp) was sliced from the gel and then DNA was recovered by passing through an Elutip-d column. After precipitation and drying, the DNA was stored in 30 μl of 10 mM Tris-HCl (pH 8.0).

The DNA (115 bp) corresponding to the NdeI-AvaII restriction fragment of hpI gene was synthetically prepared. The following double-stranded linker (SEQ ID NO:16 and SEQ ID NO:17) was formed by annealing and ligating four single-stranded oligonucleotides which were synthesized on the 380B DNA Synthesizer in a buffer (200 μl) containing 50 mM Tris-HCl (pH 7.6), 10 mM MgCl$_2$, 10 mM DTT, 50 μM ATP and 20 units of T$_4$-DNA ligase for 16 hours at 4° C.:

```
5' TATGCGTATGTTTGTTAACCAACACCTGTGCGGCTCCCACCTGGTGGAAGCTCTGTACCT
3'     ACGCATACAAACAATTGGTTGTGGACACGCCGAGGGTGGACCACCTTCGAGACATGGA

GGTGTGCGGTGAACGTGGCTTCTTCTACACCAAGCCGACCCGCCGTGAGGCAGAG      3'
  CCACACGCCACTTGCACCGAAGAAGATGTGGTTCGGCTGGGCGGCACTCCGTCTCCTG 5'
```

The ligation product was purified on a 15% polyacrylamide gel. The DNA was recovered from the gel slice electrophoretically and desalted on a Sephadex G-50 column.

About 100 pmoles of this DNA were phosphorylated in a buffer (50 μl) containing 50 mM Tris-HCl (pH 7.6), 10 mM MgCl$_2$, 10 mM DTT and ATP, as described in Brown, E. L. et al. After filtration through a column of Sephadex G-50, the DNA was stored in 50 μl of 10 mM Tris-HCl (pH 8.0).

Figure 8:
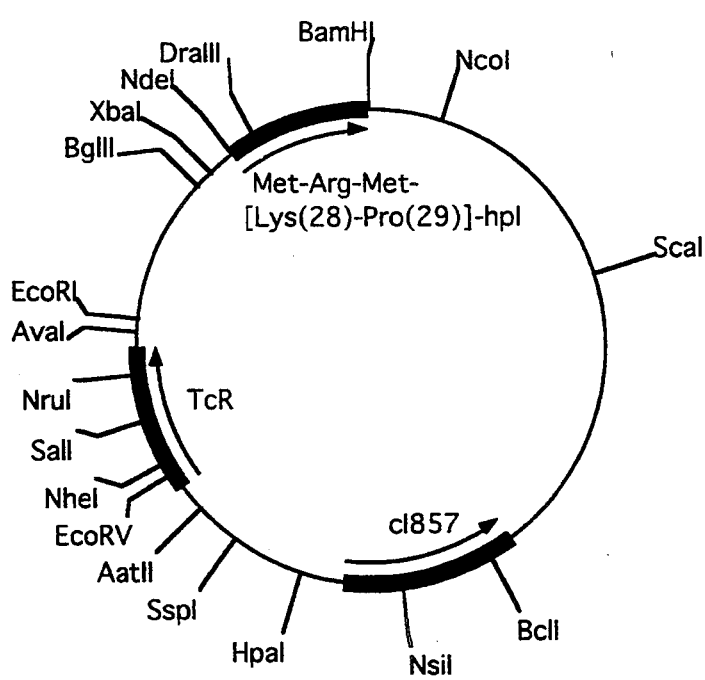
FIG. 8 is a restriction site and function map of plasmid pRB164A.

About 2.5 μl of NdeI-BamHI digested pCZR126S from Example 3B1 were mixed with 18 μl of the AvaII-BamHI restriction fragment from plasmid pRB145 and 10 μl (10 pmoles) NdeI-AvaII synthetic linker just constructed in a buffer (50 μl) containing 50 mM Tris-HCl (pH 7.6), 10 mM MgCl$_2$, 10 mM DTT, 800 μl ATP and 3.5 units of T$_4$-DNA ligase. The reaction mixture was incubated at 4° C. overnight to form plasmid pRB164A which was then transformed into *E. coli* K12 RV308 in accordance with the procedure of Example 3B4. The plasmid was amplified as described in Example 29A. A restriction site and function map of plasmid pRB164A is presented in FIG. 8 of the accompanying drawings.

B. Construction of plasmid pRB180

About 10 μg of plasmid pRB164A was cut with the restriction enzymes DraIII and NdeI in accordance with the procedure of Example 29B. The larger NdeI-DraIII restriction fragment was sliced from the gel and the DNA was recovered by passing through an Elutip-d column. After precipitation and drying, the DNA was stored in 30 μl of mM Tris-HCl (pH 8.0).

The DNA linker (40 bp) corresponding to the NdeI-DraIII restriction fragment of the LyS(B28), Pro(B29)-hpI gene was synthetically prepared by annealing SEQ ID NO:18 and SEQ ID NO:19 which were synthesized on the 380B DNA Synthesizer to form the following linker:

```
5' TATGCGTTTTGTTAACCAACACCTGTGCGGCTCCCACCTG 3'
3'     ACGCAAAACAATTGGTTGTGGACACGCCGAGGGTG      5'
```

Figure 9:
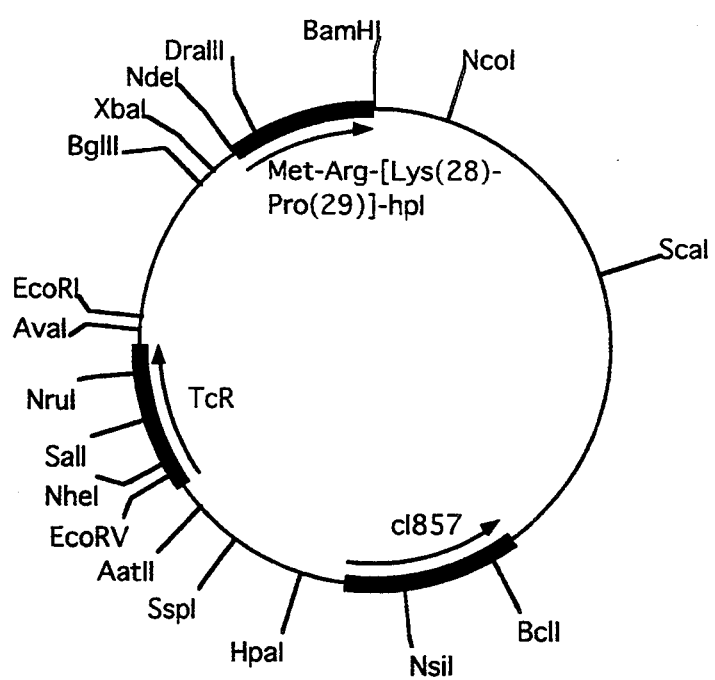
FIG. 9 is a restriction site and function map of plasmid pRB180.

After phosphorylation, about 15 pmoles of this linker was mixed with 2.5 μl of NdeI-DraIII digested pRB164A in a buffer containing 50 mM Tris-HCl (pH 7.6), 10 mM MgCl$_2$, 10 mM DTT, 800 μm ATP and 3.5 units of T$_4$-DNA ligase. The reaction mixture was incubated at 4° C. overnight and then transformed into *E. coli* K12 RV308 in accordance with the procedure of Example 3B4. The desired transformant, *E. coli* K12 RV308/pRB180, was identified by sequence analysis of its plasmid DNA. The cells were grown and protein expression was induced and quantitated as described in Example 3B4. The hpI derivative expressed has the Arg inserted amino acid at the N-terminus and residues 28 and 29 of the native sequence have been changed to Lys and Pro, respectively. Results are shown in Table 2. A restriction site and function map of plasmid pRB180 is presented in FIG. 9 of the accompanying drawings.

EXAMPLE 31

Expression of Met-Arg-[Asp(10)]-Proinsulin

A. Construction of Plasmid pRB187

About 10 μg of plasmid pRB145 were cut with NdeI and DraIII restriction enzymes and the large NdeI-DraIII restriction fragment was isolated in accordance with the teachings of Example 29B.

The DNA linker (40 bp) corresponding to the NdeI-DraIII restriction fragment was synthesized by the 380B DNA Synthesizer as before. SEQ ID NO:20 and SEQ ID NO:21 were annealed to form the following linker:

```
5' TATGCGTTTTGTTAACCAACACCTGTGCGGCTCCCACCTG 3'
3'     ACGCAAAACAATTGGTTGTGGACACGCCGAGGGTG      5'
```

Figure 10:
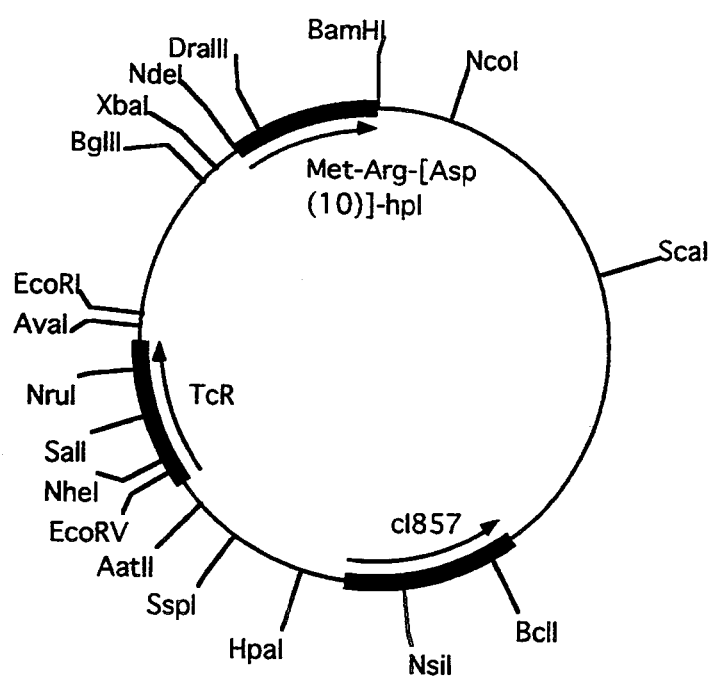
FIG. 10 is a restriction site and function map of plasmid pRB187.

After phosphorylation, about 15 pmoles of this linker was mixed with 2.5 μl of the NdeI-DraIII digested pRB145 in a buffer containing 50 mM Tris-HCl (pH 7.6), 10 mM MgCl$_2$, 10 mM DTT, 800 μM ATP and 3.5 units of T$_4$-DNA ligase. The reaction mixture was incubated at 4° C. overnight and then transformed into *E. coli* K12 RV308 in accordance with the procedure of Example 3B4. The desired transformant, *E. coli* K12 RV308/pRB187, was identified by sequence analysis of its plasmid DNA. The cells were grown and protein expression was induced and quantitated as described in Example 3B4. The expressed hpI derivative reflects the insertion of the Arg amino acid at the N-terminus and a change to an Asp residue at position 10 of the native sequence. Results are shown in Table 2. A restriction site and function map of plasmid pRB187 is presented in FIG. 10.

EXAMPLE 32

Expression of Met-Arg-[Des(33–64)]-Proinsulin

A. Construction of Plasmid DRB211B

About 10 μg of plasmid pRB145B prepared as in Example 29B was resuspended in 20 μl of 10X DraIII buffer, 20 μl of 1 mg/ml BSA, 150 μl of water, and 5 μl (15 units) of DraIII restriction enzyme. The solution was gently mixed and incubated at 37° C. for 2 hours. The DNA was precipitated with three volumes of ethanol and 0.3M sodium acetate. After centrifugation and drying, the DNA was redissolved in 20 μl of 10X BamHI buffer, 20 μl of 1 mg/ml BSA, 160 μl of water, 2 μl (20 units) of BamHI restriction enzyme and the incubation at 37° C. was continued for another one hour. The DNA was precipitated with three volumes of ethanol and 0.3M sodium acetate and electrophoresed on a 1% low melting agarose gel. The larger DraIII-BamHI restriction fragment was sliced from the gel and the DNA was recovered by passing through an Elutip-d column as described previously. After precipitation and drying, the DNA was stored in 25 μl of 10 mM Tris-HCl (pH 8.0).

Plasmid pRB145 was cut with NdeI and BamHI restriction enzymes in accordance with the procedure of Example 30A. The smaller NdeI-BamHI restriction fragment was recovered and treated with AvaII restriction enzyme in accordance with the procedure of Example 30A. The larger AvaII-BamHI restriction fragment was recovered and used below.

The DNA linker (72 bp) corresponding to the DraIII-AvaII restriction fragment of the desired gene was synthetically prepared using the 380B DNA Synthesizer. SEQ ID NO:22 and SEQ ID NO:23 were annealed to form the following linker:

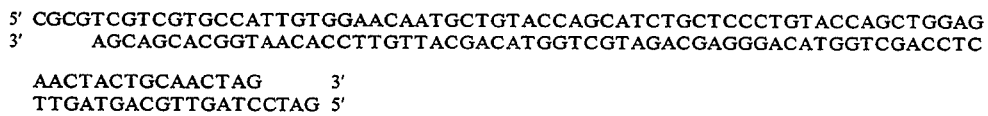

```
5'    GTGGAAGCTCTGTACCTGGTGTGCGGTGAACGTGGCTTCTTCTACACCCCGAAGACGCGTCGT
3' GACCACCTTCGAGACATGGACCACACGCCACTTGCACCGAAGAAGATGTGGGGCTTCTGCGCAGCA

GAGGCAGAG      3'
   CTCCGTCTCCTG   5'
```

After phosphorylation, about 15 pmoles of this linker was mixed with 2.5 μl of the DraIII-BamHI digested pRB145B and 13 μl of the AvaII-BamHI restriction fragment from plasmid pRB145 in a buffer containing 50 mM Tris-HCl (pH 7.6), 10 mM MgCl$_2$, 10 mM DTT, 800 μM ATP and 3.5 units of T$_4$-DNA ligase. The reaction mixture was incubated at 4° C. overnight and then transformed into E. coli K12 RV308 in accordance with the procedure of Example 3B4. The desired transformant, E. coli K12 RV308/pRB211B, was identified by sequence analysis of its plasmid DNA. The cells were grown and plasmid DNA was isolated from 500 ml cultures in accordance with the procedure of Example 1.

B. Construction of Plasmid pRB247

About 10 μg of plasmid pRB211B prepared as above was resuspended in 20 μl of 10x MluI buffer, 20 μl of 1 mg/ml BSA, 150 μl of water and 2.5 μl (25 units) of MluI restriction enzyme. The solution was gently mixed and incubated at 37° C. for 2 hours. The DNA was precipitated with three volumes of ethanol and 0.3M sodium acetate. After centrifugation and drying the DNA was redissolved in 20 μl of 10x BamHI buffer, 20 μl of 1 mg/ml BSA, 160 μl of water, 2 μl (20 units) of BamHI restriction enzyme and the incubation at 37° C. was continued for another one hour. The DNA was precipitated with three volumes of ethanol and 0.3M sodium acetate and electrophoresed on a 1% low melting agarose gel. The larger MluI-BamHI restriction fragment was sliced from the gel and the DNA was recovered by passing through an elutip-d column procedure. After precipitation and drying, the DNA was stored in 25 μl of 10 mM Tris-Hcl (pH 8.0).

The DNA linker (77 mer) corresponding to the MluI-BamHI restriction fragment of the desired gene was synthetically prepared using the 380B DNA synthesizer. SEQ ID No: 24 and SEQ ID No: 25 were annealed to form the following linker.

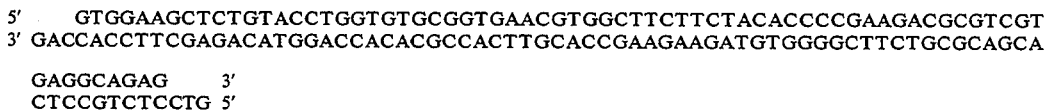

Figure 11:
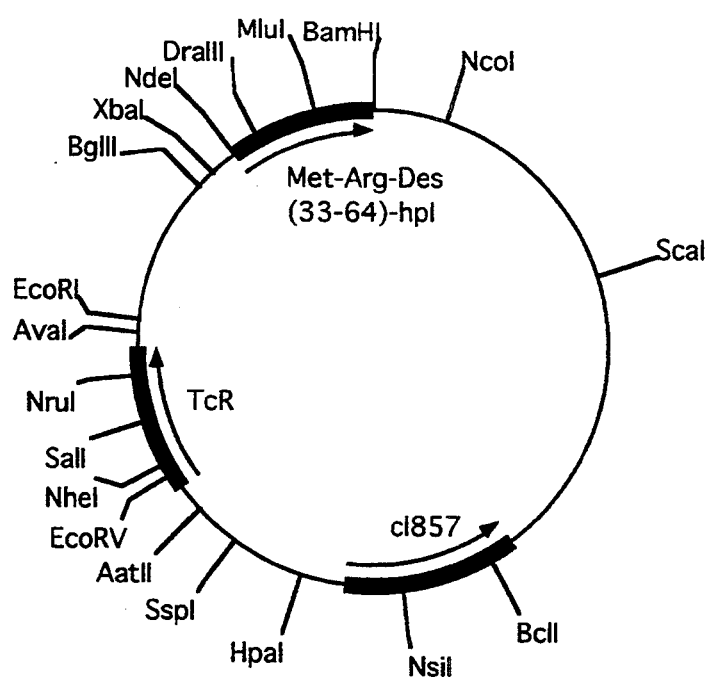
FIG. 11 is a restriction site and function map of plasmid pRB183.

After phosphorylation, about 12 pmoles of this linker was mixed with 3 μl of the MluI-BamHI digested pRB211B in a buffer containing 50 mM Tris-HCl (pH 7.6), 10 mM MgCl$_2$, 10 mM DTT, 800 μm ATP and 3.5 units of T$_4$-DNA ligase. The reaction mixture was incubated at 4° C. overnight and then transformed into E. coli. K12 RV308 in accordance with the procedure of Example 3B4. The desired transformant, E. coli K12 RV308/pRB247 was identified by sequence analysis of its plasmid DNA. The cells were grown and protein expression was induced and quantitated as described in Example 3B4. The resulting hpI derivative has an inserted Arg amino acid residue at the N-terminus and has had residues 33 to 64 removed from the C-peptide of the hpI native sequence. Results are shown in Table 2. The lower percentage of expression (4–5%) in this case, may reflect inefficient staining at low molecular weight polypeptides in a polyacrylamide gel matrix. However the level of expression is increased by about five fold as compared to the level of expression of Met-Tyr-Des (33–64) hpI (<1–2%). A restriction site and function map of the plasmid pRB247 is presented in FIG. 11 of the accompanying drawings.

TABLE 2

| Example No | Derivative | Plasmid | Expression (%) |
|---|---|---|---|
| Control | Met-hpI | pRB/hpI | <3 |
| 29 | Met-Arg-hpI | pRB145B | 12–13 |
| 30 | Met-Arg-Lys(B28),Pro(B29)-hpI | pRB180 | 12–13 |
| 31 | Met-Arg-Asp(B10)-hpI | pRB187 | 14.6 |
| 32 | Met-Arg-Des(33–64)hpI | pRB247 | 4–5 |

EXAMPLE 33

Construction of RV308/pIGF2

The synthesis of the coding region of the Met-Arg-IGF-II gene (SEQ ID NO:26 and SEQ ID NO:27) was accomplished in accordance with the teachings of Example 3. The synthetic gene contained NdeI and BamHI restriction enzyme sites at the 5' and 3' termini, respectively, to facilitate the cloning experiments.

Figure 12:
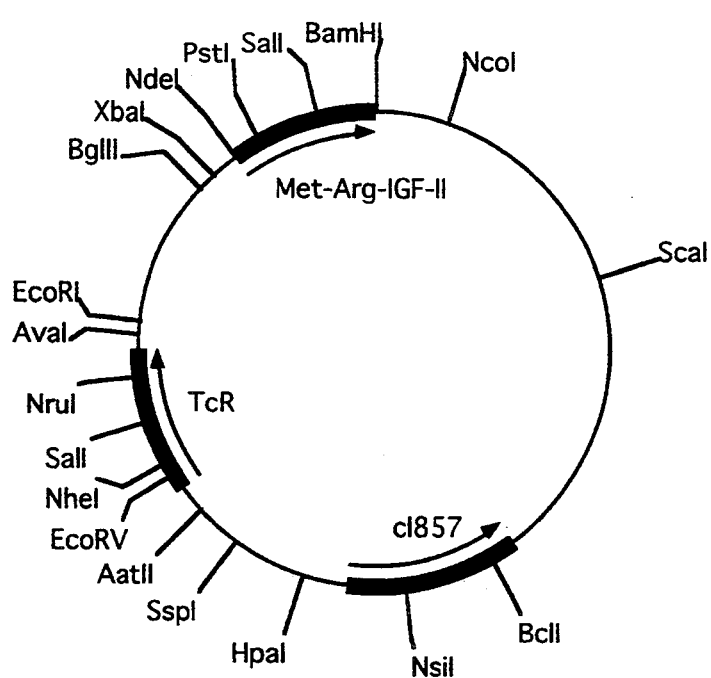
FIG. 12 is a restriction site and function map of plasmid pIGF-II.

About 2.5 μl (6 pmoles) of the synthetic gene was mixed with 3 μl (0.25 pmoles) of the NdeI-BamHI vector fragment produced in Example 3B1 in 5 μl of 10X Ligase Buffer, 4 μl of 10 mM ATP, 0.5 μl of 1M DTT, 35.5 μl of water and 2.5 units of T$_4$-DNA ligase. The reaction mixture was incubated at 4° C. overnight and then transformed into E. coli K12 RV308 in accordance with the procedure of Example 3B4. The desired transformant, E. coli K12 RV308/pIGF2, was identified by sequence analysis of its plasmid DNA. The cells were grown and protein expression was induced and quantitated as described in Example 3B4. Met-Arg-IGF-II was expressed as 22% of the total protein expressed by the cells. A restriction site and function map of plasmid pIGF-II is presented in FIG. 12 of the accompanying drawings.

---

We claim:

1. A method of recombinantly producing a polypeptide derivative, said method comprising: constructing a recombinant DNA vector; transforming a prokaryotic host cell with said vector; and culturing said transformed host cell under conditions suitable for gene expression; wherein said vector comprises:
   A. a DNA sequence that provides for autonomous replication or chromosomal integration of said vector in a prokaryotic host cell;
   B. a promoter and translational activating sequence functional in said host cell;
   C. an arginine codon inserted immediately 3' to said translational activating sequence; and
   D. a DNA molecule that is operably linked to vector elements A, B, and C such that the structure of the resulting polypeptide derivative is Methionine-Arginine-R, wherein R is selected from the group consisting of IGF-I, IGF-II, proinsulin, insulin A chain, insulin B chain, GRF, and somatostatin.

2. A method of claim 1 wherein R is IGF-I.
3. A method of claim 1 wherein R is IGF-II.
4. A method of claim 1 wherein R is proinsulin.
5. A method of claim 1 wherein R is insulin A chain.
6. A method of claim 1 wherein R is insulin B chain.
7. A method of claim 1 wherein R is GRF.
8. A method of claim 1 wherein R is somatostatin.

* * * * *

UNITED STATES PATENT AND TRADEMARK OFFICE
CERTIFICATE OF CORRECTION

PATENT NO. : 5,378,613

DATED : January 3, 1995

INVENTOR(S) : Rama M. Belagaje

It is certified that error appears in the above-indentified patent and that said Letters Patent is hereby corrected as shown below:

Column 3, line 59, "PL promoter" should read -- $P_L$ promoter --.

Column 4, line 52, "lambda PL" should read -- lambda $P_L$ --.

Column 12, line 3 of column Strains/RV308 in table 1, "RES106G1" should read -- RB5106G1 --.

Column 12, line 9 of column Expression %/RV308 in table 1, "19.9" should read -- 18.9 --.

Column 12, line 38, "DRB145" should read -- pRB145 --.

Column 13, line 5, "HCL 8.0)" should read -- HCL (pH 8.0) --.

UNITED STATES PATENT AND TRADEMARK OFFICE
CERTIFICATE OF CORRECTION

PATENT NO. : 5,378,613

DATED : January 3, 1995

INVENTOR(S) : Rama M. Belagaje

It is certified that error appears in the above-indentified patent and that said Letters Patent is hereby corrected as shown below:

Column 14, line 2, "HCL 8.0)" should read -- HCL (pH 8.0) --.

Column 16, line 27, "CCCACCTG 3'" should read -- CCGACCTG 3' --.

Column 16, line 28, "GGGTG 5'" should read -- GGCTG 5' --.

Column 16, line 51, "DRB211B" should read -- pRB211B --.

Column 18, insert under "Table 2", -- Expression Levels of Proinsulin Analogs

Signed and Sealed this

Twenty-eighth Day of November 1995

Attest:

BRUCE LEHMAN

Attesting Officer

Commissioner of Patents and Trademarks